United States Patent
Majumdar et al.

(10) Patent No.: US 10,739,351 B2
(45) Date of Patent: Aug. 11, 2020

(54) FUNCTIONAL CHARACTERIZATION OF IMMUNE REPERTOIRES

(71) Applicant: California Institute of Technology, Pasadena, CA (US)

(72) Inventors: Devdoot Majumdar, Redondo Beach, CA (US); Anirudh Mathukumilli, Highlands Ranch, CO (US); David Baltimore, Pasadena, CA (US)

(73) Assignee: CALIFORNIA INSTITUTE OF TECHNOLOGY, Pasadena, CA (US)

( * ) Notice: Subject to any disclaimer, the term of this patent is extended or adjusted under 35 U.S.C. 154(b) by 478 days.

(21) Appl. No.: 15/729,253

(22) Filed: Oct. 10, 2017

(65) Prior Publication Data

US 2018/0100863 A1 Apr. 12, 2018

Related U.S. Application Data

(60) Provisional application No. 62/406,115, filed on Oct. 10, 2016.

(51) Int. Cl.
| | |
|---|---|
| *G01N 33/68* | (2006.01) |
| *C12N 15/10* | (2006.01) |
| *C12Q 1/6876* | (2018.01) |

(52) U.S. Cl.
CPC ..... *G01N 33/6854* (2013.01); *C12N 15/1037* (2013.01); *C12N 15/1055* (2013.01); *C12Q 1/6876* (2013.01); *G01N 33/6878* (2013.01)

(58) Field of Classification Search
CPC ............ C12N 15/1037; C12N 15/1055; C12Q 1/6876; G01N 33/6854; G01N 33/6878
See application file for complete search history.

(56) References Cited

U.S. PATENT DOCUMENTS

| | | | |
|---|---|---|---|
| 2009/0068170 A1 | 3/2009 | Weitz | |
| 2015/0275296 A1* | 10/2015 | Klinger | ................ C12Q 1/6881 |
| | | | 506/9 |
| 2019/0025299 A1* | 1/2019 | Vigneault | .......... C07K 14/7051 |

(Continued)

FOREIGN PATENT DOCUMENTS

WO WO 2016/040476 A1 3/2016

OTHER PUBLICATIONS

Briggs, A.W., et al., Tumor-infiltrating immune repertoires captured by single-cell barcoding in emulsion, bioRxiv, pp. 1-34, 2017.
(Continued)

*Primary Examiner* — Jeremy C Flinders
(74) *Attorney, Agent, or Firm* — Knobbe, Martens, Olson & Bear LLP

(57) ABSTRACT

Provided herein are method and kits for elucidation of immunological repertoires (comprising functional pairs of immune cell receptors and antigens). In some embodiments, an immune cell receptor and an antigen that it binds to are isolated, and sequence information is obtained about the immune cell receptor and antigen. In some embodiments, an antigen expressed on a first cell and an immune cell receptor expressed on a second cell can form a synapse, mRNAs can be isolated from the resulting doublet of cells, and sequences of the functional immune cell receptor and its antigen can be obtained from the mRNAs.

22 Claims, 22 Drawing Sheets

Specification includes a Sequence Listing.

(56) References Cited

U.S. PATENT DOCUMENTS

2019/0101537 A1* 4/2019 Weitz ............... B01L 3/502792

OTHER PUBLICATIONS

Chailyan, A., et al., The association of heavy and light chain variable domains in antibodies: implications for antigen specificity, FEBS Journal, vol. 278, No. 16, pp. 2858-2866, 2011.

Dash, P., et al., Paired analysis of TCRα and TCRβ chains at the single-cell level in mice, The Journal of Clinical Investigation, vol. 121, No. 1, pp. 288-295, 2011.

Dekosky, B.J., et al., High-throughput sequencing of the paired human immunoglobulin heavy and light chain repertoire, Nature Biotechnology, vol. 31, No. 2, pp. 166-169, 2013.

Dou, D., et al., Type II transmembrane domain hydrophobicity dictates the cotranslational dependence for inversion, Molecular Biology of the Cell, vol. 25, No. 21, pp. 3363-3374, 2014.

Fischer, N., Sequencing antibody repertoires: The next generation, mAbs, vol. 3, No. 1, pp. 17-20, 2011.

Georgiou, G., et al., The promise and challenge of high-throughput sequencing of the antibody repertoire, Nature Biotechnology, vol. 32, No. 2, 2014.

Gunzer. M., et al., A spectrum of biophysical interaction modes between T cells and different antigen-presenting cells during priming in 3-D collagen and in vivo, Blood, vol. 104, No. 9, pp. 2801-2809, 2004.

Klein, A.M., et al., Droplet Barcoding for Single-Cell Transcriptomics Applied to Embryonic Stem Cells, Cell, vol. 161, No. 5, pp. 1187-1201, 2015.

Macosko, E.Z., et al., Highly Parallel Genome-wide Expression Profiling of Individual Cells Using Nanoliter Droplets, Cell, vol. 161, No. 5, pp. 1202-1214, 2015.

Mazutis, L., et al., Single-cell analysis and sorting using droplet-based microfluidics, Nature Protocols, vol. 8, No. 5, pp. 870-891, 2013.

McDaniel, J.R., et al., Ultra-high-throughput sequencing of the immune receptor repertoire from millions of lymphocytes, Nature Protocols, vol. 11, No. 3, pp. 429-442, 2016.

Nikolich-Zugich, J., et al., The many important facets of T-cell repertoire diversity, Nature Reviews Immunology, vol. 4, No. 2, pp. 123-132, 2014.

Qi, H., et al., SAP-controlled T-B cell interactions underlie germinal centre formation, Nature, vol. 455, No. 7214, pp. 764-769, 2008.

Von Boehmer, L., et al., Sequencing and cloning of antigen-specific antibodies from mouse memory B cells, Nature Protocols, vol. 11, No. 10, pp. 1908-1923, 2016.

* cited by examiner

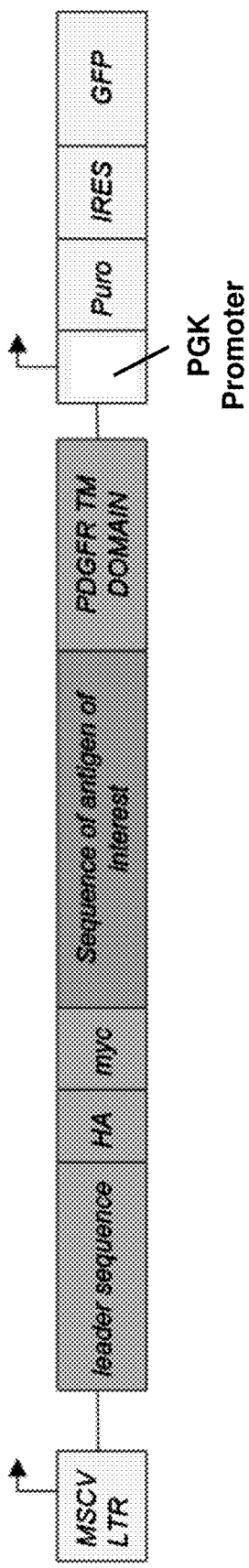

FIG. 9

ATGAACCCTAACCAAAGATCATCACCATCGGCAGCGTGTGCATGA
CCATAGGCATGGCCGCACTGATCCTGGCCATTGGCGCAATCATCAG
CATCTGGATCAGCCACAGCATCCAGTTGGGCAACCAGAATCAAATC
GAGACCTGCAATCAGTCTGTTATCACCTACGAGAACAACACCTGGG
TGAACCAGACTTACGTGAACATCAGCggcagctaccctacgatgtcccgactat
gccggaggaagtgaacagaagttgatcagcgaggaggacctgaaggtgttcggcaggtgcgag
ctggctgccgccatgaagaggcacggcctggataactacagggggtacagcctgggcaactggg
tgtgcgccgctaaattcgagagcaacttcaatacgcaggccaccaacaggaacaccgatggctct
actgactacggcatcctgcaaatcaactccagtggtggtgtaacgaggcaggacccctggaag
caggaacttgtgcaacatccatgcagacgcagcgacatcaccgccagcgtgaact
gcgccaagaagatcgtgtcaggctgcaggctgcaacggcatgaacgcctgggtggcatggaggaacaggt
gcaaggggaccgacgtgcaggcttggatacgcggctgtcgacttggatcaggcaggcggttaa
(SEQ ID NO: 23)

FIG. 10 atggagaccgacacctgttgctgtgggtactgctcctgggtgcccggcagcaccggcgacggg
ggcagctaccctacgatgtgccgactatgccggaggaagtgaacagaagttgatcagcgagga
ggacctgaaggttcggcaggtgcgagctgccatgaagaggcacggcctgataact
acaggggtacagcctggcaactggtgtgccgctaaattcgagagcaacttcaatacgcag
gccaacacaggaacaccgatggctctactacggcatcctgcaaatcaactccaggtggtg
gtgtaacgacgggcaggacccctggaagcaggaactgtcaacatccatgcagccctgctga
gcagcgacatcaccgccagcgtgaactgccaagaagatcgtcagacgcaacggcatga
acgcctgggtggcatggaggaacaggtcaaggggaccgagtcagggccagcttgatacggctg
tcgacttggatcaggcaggttcaggtccctttcaaggttgtgtgatcagctatcctggcactgtgctg
atcgtggtgcctcatagcctcccttcaaggttgtgtgatcagctatcctggcactgtgctgtgctgac
catcatcagcctgataatactgattatgttgtggcagaagaaacctagg (SEQ ID NO: 24)

FIG. 11 tgaaagaccccacctgtaggtttggcaagctagcttaagtaacgccattttgcaaggcatgaaaatacataactgagaatagagaagttcagatcaaggttagaacaga
gagacagcagaatatggccaaacagatatcgtggtaagcagttcctgcccgctcaggccaagaacagatgtccccagatgcggtcccgcctcagcagtttct
agagaaccatcagatgtttccaggtgcccaagacctgaaatgaccctgcctttattgaactaaccaatcagttgcttctgttcgcggcttctgctcccgag
ctcaataaaagagcccaaccccctcactcgcgcgcagtcctccgatagactgcgtcgcccggtaccgtattccaataaagcctctgctgtttgcatcgaatcgtg
gactgctgatccttggagggtcctcagattgattgactgcccacctggggtctttcatttgagttccaccgagatttgccctgcgtcgtactagttagctaactagctgta
cccgccggagtaagctggccagcgtgcagagttcgcggtcgttcgtgtctcgtctcgtcctcaggagacttcgccctgtactagttagctaactagctgta
tctggcggaccgtggtgaactgcgacgagttcgacaaccgccgacaacctcccaggagctccaggacttcgggcccgttttgggcccgacctgaggaaggag
tcgatggaatcgaccccgtcgcagcatcgttcgtctgtcgtctctgtcgactgtgttctgtatttgtcgaaaattagggccagacttgttaccactccttaagtttgaccttagtcactgg
cttgtctgcagcgtcgcagcatcgttcgtctgtcgtctctgtcgactgtgttctgtatttgtcgaaaattagggccagacttgttaccactccttaagtttgaccttagtcactgg
aaagatgcagcgatcgtcacaaccagtcgtagaagatcgtcaagaagagacgttggtacctctgctcgcgaatgccaaccttaacgtcgatgccgcgagac
ggcaacttaaccgagacccatcatcaccagttaagatcaaggtcttttcacctgccgcatgaccgagtcctccatccgccccgtctccctgacctctgctgaagccttggcttt
tgaccccctccctggtcaagcctttgtacacccttaagctccctccgctcttcctcactccctgttcgacccgcctcgtgaccccgtcgatcctccctt
tatcagcctcactcctttctagccgcactgtgatcgccgaattagatctgccATGAACCCTAACCAAAAGATCATCACCATCGGGCCAGCGTGCATGAC
CATAGGCATGGCCGGCCACTGTGCCGATCCTGCCAATCAGTCTGTTATCCACCTACGAGAACAACACCTGGGTGAACCAGACTTACGT
AACCAGAATCAAATCGAGACCTGCAATCAGTCTGTTATCCACCTACGAGAACAACACCTGGGTGAACCAGACTTACGT
GAACATCAGCggcagctaccttacgatgtgccgactatgcggagaagaagtgaacagaagttgatcagcgaggaggaccttgaaggttgcgagagt
ggctgccgccatgaagagaggccaccggctgataactacaggggtacagccggggcaactgggtgtgccgctaaattcagagagcaagcaggccaacaa
caggaacaccgatgctctactgactacgcatcctgcaaatcaactccaggtggtgtaacgacggcaggaacctgaagcaggaactgtgcaacatcccatgc
agcgccctgctgagcagcgacatcacccgccagctgaactgcgacgtgaatcgtcagagcgtgaacgctggcatggaggaacaggtgca
agggaccgactgcaggctttcaggccgggctgttgatacgccgcagcgtgaagcagttaactcgaagttaccgcggtaggagaggcgttccaaggcagt
ctgaacgatgcgcttagcagccgctttcggccaactttccacatccaggtgcctgcctccacgcgccaaccggctccgtctttggt
ggccccttcgccaccttactctcccagccaaggaattcccctagtcaggaagtggccatttgcctccttcgctttgggctcagaggctggaagggtgggt
gcagatgacagccgctgagcagcaatgaagagccgttaggctttggggcgcagccgaagttctcgaaggcccggcatttgcacgcttcaaaagcacgtgccgcgttct
cggggggctcaaggtcaggccgggggccgggctcagccctgcagcccccaagctctccgaggccgccaaagtctcaggccgcatttgcacgcttgccgcgttct
cctcttccatctccggccttgacctgcagccaagttaccatgaccgagtacaagcccacgcgctgccaccggctacagccccgacgactcccaggccgtacgac
ctcgccgccgcgttcgccgactaccccgcgactacccgctggcagcccaagagtcccaatgacgtgtcgtcgcaggagtcgccaatagcacgtctcactagtctgt
ctgacatcggcaagttggtcggacgacggcgcgcggcagtgggtcgaagctcggaccaggctcgagagcgtcgaagagcgtcgaagaacttcctccacgcgcgtggg
ctcgacatcggcaagttggtcggacgacggcgcgcggccaagtggcagacgacggcgaacgtcgaagcgcgcggaaggcgcgacggcgctgggcagccgcgc

FIG. 11 continued

```
gcatggccgagttgagcggttcccggctggccggcgcagcaacagatgaaggcctcctggccgccgcaccggccgcggttcctggccacgtcgcg
tctcgccgaccaccaggcaagtctggcagcgccgtcgctgtcccgagtgaggcgccgggtccccggccttcctgagacctccgcgccc
gcaactccccttctacgagcgccgctcggcttcaccgccgacgtcgaggtgcccgaaggaccggcatggtgcatccaagccccggtgctgacgcc
gccccacgaccccgagcgccgaccgaaaggagcgcacgacccccatgcatccaattcgccccccccctaacgttactggccgaagcgcttgaataaggcgg
tgtgcgtttgtctatatgttattttccaccatattgccgtcttttggcaatggaggccccgaaacctgcctgtcttcttgacgagcattccctagggtcttcccctcgccaaa
ggaatgcaaggtctgttgaatgtcgttgaagaagcagttcctggaagcttcttgtagcgaccttgcaggcagcggaaccccaccctggc
gacaggtgcctcgccgcaaagccacgtataagatacaccgcaaaggcgcacaaccccagtgccacgttgtgagttgtgatagttgtggaaagagtcaaatggct
ctcctcaagcgtattcaacaagggctgaaggatgcccagaaggtaccccattgtgatctgggcctcggtgcacatgcttacatgtgttagtcgaggttaaa
aaacgtctaggcccccgaacacgggacgtgtttcctttgaaaaacacgatgataatatgccacaaccatgtgacaaggcgagagcctgttcacgggt
ggtgcccatcctgtcgagctgcgacggcgcgacgtaaacgccacaagttcagcgtgtctgcgaggcgaggcgatgccacctacggcaagcctgacctgaagtcatc
tgcaccaccgcaagctgcccgtgcccctgaccctcgtgaccacctgaccctcagcgcgtcagtgcttcagcgcgctaccccgccgagtgaagttcgagggcgaccctggt
caagtccgcaagtcccgaaggctacgtccaaggagctacgtccaggagcgcaccatcttcaaggacgacgcaactacaagacccgcgagtgaagttcgagggcgaccctggt
gaaccgcatcgagctgaagggcatcgacttcaaggaggacggcaacatctgggcacacaagctggagtacaactacaacagccacaacgtctatatcatgccgaca
agcagaaacgcatcaaggcgaacttcaagatcgccacaacatcgccctgagcaccgccgagaagcgccatcacatgcgatcacatgtcctgcgagttcgtgaccgcg
gccgtgctgctgccgacaaccactacctgagcacccagtcggccctgagcaagagaccccaacgaagaccccaagagaagcgatcacatgtcctgcgagttcgtgaccgcg
ccgggatcactctcggcatgacgagctgtacaagtgtacaagaccccacctgtagttggcaagcatagcttcaaggcatgaaaataatactgagaatagag
attagtctccagaaaaaggggagaacagagagcagaaccatcagatgtttcaggtgccaaacaggatttgcccccaaccctgccttatttttgaactaacaatcagttcgttctcg
aagttcagatcaaggttaggaacagagagacagagaaccatcagatgtttcaggtgcccaagatgaaatgaccctgccttattgaactaaccatcagttcgttctcg
cttcgttcgcggcttctgcatccgactctgtgtctcgtgttccgagctcaataaagagcccacaaccctcactcgcgccagtcctcgatagactgcgtgccccgtaccctgtatccaataa
accctctcagttcagttgcatccgactctgtgtctcgtgttccgagctcaataaagagcccacaaccctcactcgtgattgatcactccctcagcgggtgtttcatggtaacagttttcttgaagttgag
aacaacattctgaggtaggagtcgaattcgtaatccttgactcactgtttgaatccatcaatattagccacatagccacatcaaattactctgaaatagttcattatggacagcgcagaag
agctgggagaattaattcgtaatcatgtcatagctgtttcctgtgaaattgttatccgctcacaattccacacaacatacgagccgaagcataaagtaaaagctggg
gtgcctaatgagtgagctaactcacatttaattgcgttgcgctcactgcccgctttccagtcgggaaacctgtcgtgccagctgcattaatgaatcggccaacgcggggaga
ggcggtttgcgtattgggcgctcttccgcttcctcgctcactgactcgctgcgctcggtcgttcggctgcggcgagcggtatcagctcactcaaaggcggtaatacggttatcca
cagaatcaggggataacgcaggaaagaacatgtgagcaaaaggccagcaaaaggccaggaaccgtaaaaaggccgcgttgctggcgtttttccataggctccgcccc
```

FIG. 11 continued cctgacgagcatcacaaaaatcgacgctcaagtcagaggtggcgaaaccgacaggactataaagatacccaggcggttcccctggaagctccctgtgcgctctcctgtt
ccgacctgccgcttaccggatacctgctccgcttcagcccgttcacgcccgaacccgttcagccgacgtgcgccttatcgctgagtccaaccggtaagacacgacttatcgccactggccagcagccactg
ggctgtgcacgaaccccgttcagccgacgtgcgccttatcgctgagtccaaccggtaagacacgacttatcgccactggccagcagccactg
gtaacaggattagcagagcgagagttggtagggcggtgctacagagttcttgaagtggtggcctaactacggctacactagaaggacagtattggtatctgcgctgctgaag
ccagttaccttcgaaaaagagttggtagctcttgatccgcaaacaaccacccgctgtagcggtgttttttgtttgcaagcagcagattacgcagaaaaaggatc
tcaagaagatcctttgatcttttcacggggtctgacgctcagtgaacgaaaactcacgttaaggattttggtcatgagattcaaaaggatcttcacctagatcttttaaa
ttaaaaatgaagttttaaatcaatctaaagtatatgagtaaacttgtctgacagttaccaatgcttaatcagtgaggcaccatctcagcgatctgctcatttcgttcatccatag
ttgcctgactcccgtcgtgtagataactacgatacggagaggcttaccatctgccccagtgctgcaatgatcaccgagacccactcaccgctccagatttatcagc
aataaaccagccagccgcggagccggagcgagcagaagtggtcctgcaactttatccgcctccatccagtcttattaattgtgcggaagctagagtaagtagttgccagtt
aatagtttgcgcaacgttgttgccattgctacaggcatcgtgctgtgtcacgctcggtcattcagctccggttcccaacgatcaaggcagttacatgatccccc
atgttgtgcaaaaaagcggttagctccttcggtgcctccgatcgttcagaagtaagttgccgcagtgttatcactcatgttatgcagcactcttccoggtcaatacggataatacccgccc
catccgtaagatgctttctgtgactggtagtactcaaccagtcatcattctgagaatagtatgcgggaccgagttgctccccggtcttgccccggtcaatacggataatacccgcc
acatagcagaacttaaaagtgctcatcattgaaaaacgttcctcgggggcgaaactctcaaggatcttaccgctgttgagatccagttcgatgtaaccactcgtgcacccaa
ctgatcttcagcatcttttacttcaccagcgtttctggtgagcaaacaggaaggcaaaatgccgcaaaaaaaggaataaaataaacaaataggggttccgcgcacattccccgaa
actctccttttcaatatattattgaagcattatcaggttattgtctcatgagcgtatcacgaggcccttcgtctcgcgtttcggtgatgacggtgaaaacctct
aagtgccacctgacgtctaagaaaccattattatcatgacattaacctataaaataggcgtatcacgaggcccttcgtctcgcgtttcggtgatgacggtgaaaacctct
gacacatgcagctcccggagacggtcacagttgtctgtaagcggatgccggagcagacaagccgtcaggcgcgtcagcggtgtttggcgggtgtcggggctggct
taactatgcggcatcagacgcagattgtactgagagtgcaccatatgcggtgtgaaatacccgcacagatgcgtaaggagaaaataccgcatcaggcgccattcgccattca
ggctgcgcaactgttggaaggcgatcggtgcggccctttgctattacgccagctggcgaaagggggatgtgctgcaaggcgattaagttgggtaacgccaggttttc
ccagtcacgacgttgtaaaacgacggccagtgagcgcgcgtaatacgactcactatagggcgaattgggcccgacgtcgcatgctcccggccgccatgaccgagatcg
aagcgctcatgagcgcgaagtgcgagccgatcttccccatcgtgatgtcgcgatatcagtgtcgcgatataggccccagcaaccgcacctgtggcgccggtgatgccggccacgatcg
tcgggctgagaggcgattagtcgtcgaattttgttaaagacaggatatcagtgtcttcaggctctagttttgactcaacaatatcaccagctgaagctcaacgactagagccatagat
aaaataaaagattttattagtctccagaaaaaggggggaa (SEQ ID NO: 25)

FIG. 12 tgaaagacccacctgagtttggcaagctagcttaagtaacgccattttgcaaggcatgaataagcatgagaatagagaagttcagatcaaggttaggaacaga
gagacagcagaatatggccaaacagatctgtggtaagcagttcctgcccagtcccagatggtcccagatgcggtcccgcccttctgtgctccccgag
agaaccatcagatgtttccaggtgcccaaggacctgaaatgacccctgccttattgaactaaccaatcagttcgcttcgtctgttcgcgcttctgctcccgag
ctcaataaaagagcccacaaccccctcactcgcgcgcagtcctccgatagactgcgtcgccggtaccgtattccaataaagcctctgtgtttgcatcgaatcgtg
gactgctgatccttggagggtcctcagattgattgactgcccaacctcggggtctttcatttggagttccaccgagatttgcgcctgcgtctatttgagaccaacgaccc
ccccgcggagtaagctggcagagtcgagttcagagctcccaggacttccaagagtcccgcaacccctgcgtgtctctggcctgtactagtagctagctctgta
tctggcggacccgtgtgaactgcgacgagttcgacaacccctggggcgccgttcagacaaacagtccccgtcccgtcgtaatttgctttcggttggaaccgaagcgcgt
tcgatggaatccgaccgctgcagcatcgttcgtttcgtctctgtactgttcttgtctgatttctgtatttctgaaaataggccagactgttaccactccttaagttaccttaggccactgg
ctgtctgcgcagccgcgcgatgcgctcacaaccagtggttaccttctgtctgcagaatgccaacctttaacgtcgatgcgcgagac
aaagatgcgacggatcgctcacaaccagtgctagagtcaaggaagacgtttggatcttttcacctgaccatggccgatggccatgcccatcgctgcaccaacctgtgatgaagttttgctttt
ggcaccttaaccagaacccatcatccaaggttaagatcaaggtctttttcacctgcctcttcgcctcttcccctgacccctcctgtcaacatcgatccgatcctcctt
tgaccccccctcggtcaaacctttcaagccctttgtacaccttagccctttgtacaccttagccctttgtacaccttagccctttgtacaccttagccctttgtacaccttagccctttgtacaccttagccctttgta aagttgtgatcagtctccgactgcgtcagctatgcgactgtgtgctgacctatcagcctgataaactgattatgttgcagaagaaactaggtaactgaggtataacgaattct
acgggtagggaggcgctttccaaggcgtcgttctttgtggccaacggtcgttcttgtggccaacggtcgttctttgtggccaacggtcgttctttgtggccaacggtcgttct
caccggctagggcgcaacccggctccgttcgtttgtggccaacttcctcactcctccttagcagccccttagcagccccttagcagccccttagcagcccctg
tgacaaatggaagtagcacgtctcactagtctcgtcagatgacacagccagtggaagagcgggtagccttgggcagcggccaatagcagcttctcctc
gctttctggctcagggctggaggttggtccaggggcccccc cacgcttcaaaagcgcacgtctgccgccgctgtctgtctttctcctcttcctcatctccgggcctttcacctgctgtccctcatcctg
caccccgacgacgtcccaggacccccatcatcacgcccatctcctcggcctgcgaccatgaccagcagccacccgcgcctcaagccacgccacggtgcctgcgccacatcgagcggtca
ccgagctgcaagactcttcctcacgcgctctggcccgagttgagccgagttgagccgttcccggttcccggttcccgg aagcggggcgtgttccgcgagatggccgagcatggccgcgcagcaacagatgcaagcccacccggcgccgaccggcc

FIG. 12 continued aaggagcccgctggttcctggccacgtcggcgtctgccgaccaccaggggcaaggtctggcagccgcctgtcgtcccgagtggaggcggccagcgcgc
cggggtgcccgcttcctgagacctccgcgccccgcaacctcccttcacgagcgctcgcttcaccgtcaccgcgagtcgagtgccgaaggaccgcgcacct
ggtcatgaccgcaagcccggtcctgaacccgagcccgaccaagagagcgcagaccccatgcatcaattcgcccccccta
acgttactggccgaagccgcttgaataaggccggtgcgttgtctatatgttatttccaccatatatccgtctttggcaatgtgaggcccgaaacctggccctgtctcttg
acgagcattcctaggggtcttccccctctcgcaagaatgcaagtctcttgaatgtcgttgaaggaagcagttcctggaaagcttcttgaagacaaacgctgtagc
gaccctttgcaggcagcggaaccccccacctgcgacagtgcctcgcccaaagccacgtgataagatacacctgcaaaggcgcacaaacccagtgccacgt
tgtgagttggatagttgtggaaagagtcaaatgctcctcaagctcctcaagctattccaagaggggctgaaggatgccagaagggtaccccattgtatggggatctgatctgggcctc
gcacacatgcttacatgtgtttagtcgaggtcgagttgttcaccggggtgttgccatcctgtcgagctgagagctcgagtagtcagttcagtcttcagcc
gtgagcaaggcgagggagctgttcaccctgaagttcatcgaccgctcttcaagtccgcaagcgcatgaacgcaagaacgcaacatcacaagacccg
atgccacctacggcaggcaagctgaccctgaagttcatcgaccgctcttcaagtcgcaagcatgaacgcaagaacgcaacatcacaagacccg
gctaccacgaccacatgaagcagcacacctgagttcgagggcgacaccctgtgaacgcatcgagctgaacgcagagaacaagcatcaaggaagcacaagaacgcaacaagctgagtacaact
cgccgagtgaagtcgagggcgacacctgtgaacgcacagagaacaagcatcaagatcgacccgcgacaccgtgaactttcaagatatctgaggacgcagcaagtcgagcaagcagctgcagctgcgtcgcga
acaacagcacacagacagaaccacaaccccatcggcacggcaaggccgcgatccgccgacaaccacctaccggcgtgtgagactacaagtaattattatccgccgcaccagtcgagagacccgcgacacaagagaagc
ccactacaagagcacacgaacagaaccccatcggcacggcaaggccgcgatccgccgacaaccacctaccggcgtgagagactaagaattatcaagcttatcgatccgtcgac
gatcacatgtcctgctgagttcctgtgaccgccgggatcactctcggcatgacgagctgtacaagtaagtcaagttcatcaaaggagaccccctgagttggcaagctagcttaagtaacgccatttg
caaggcatgaaaatacataactgagaacagatcagttcgcttccccaagatcaaggttagaacagagaagaacagagaacatcagatgttccaggtgcccaaggacctgaaatgacc
gcccggctcagggccaagacagatgtcccagatgcgttccccagatcgcgtcgttcccgccttctgttccgcgcttcgcggcccaaccccctcactggccgccgagtcctcga
tagactgcgtcgcccggtaccgtgtatccaataacccctcttgagttgtcatccgactgctggtgttctcctgaggtctcctcgagtgattgactaccgtcagcg
gggtctttcatggtaacagttcttgaaggtgagaacacatttgaggtaggagaacatccttgaatccgactcaattgagttccctgtaaattccagcacatactccaat
actcctgaaatagttcattatgacagcgagagagctgggtgggccttaatgagttgtaaactgtaactcgccattaattcgttgcgctcactcgctcgtgtgaaacctgtgccag
tacgagccggaagatagagaaagtgtaaagcctggggtgtaaagcctggggtgtaaagcctggtattgcattgcgctatttgcattgcgctcttcctgctactgactgcgcttgcgctgcgcgagcggta
ctgcattaatgaatcggccaaccgcgcgggagaggcggttgcattgcgctatttgcattgcgcttgccattgggcttgcgctatttgcattgcgctctggcgtcaccaagatgcttgcgctatttgcattgcgctctggcgtcaccactgaccctgctgcggtcgcgccgagcggta
tcagctcactcaaaggcggtaatacggttatccacagaatcaggggataacgcaggaaagaacatgtgagcaaaaggccaggaaccgtaaaag
gccgcgttgctggcgttttccataggctccgccccctgacgagcatcacaaaaatcgacgctcaagtcagaggtggcgaaacccgacaggactataaagataccaggc
gtttccccctggaagctccctcgtgcgctctcctgttccgaccctgccgcttaccggatacctgtccgcctttctcccttcgggaagcgtggcgctttctcatagctcacgctgtagg

FIG. 12 continued tatctcagttcgtgtagtcgttcgctccaagctggctgtgtgcacgaaccccgttcagcccgctgcgcctatcgtacatcgtcttgagtccaacccgtaa
gacagacttatcgctgccactggcagcagccactggtaacaggattagcagagtgaggcgagttaggcgtcttgaagtgtggcctaactacggctacacta
gaaggacagtatttggtatcgctgctctgaagccagttaccttcgaaaaagagttgtagctcttgatccggcaaacaaccaccgctgtagcgtggtttttgttgc
aagcagcagattaccgcagaaaagattcaagaagatctcaagagatcctttgatctttctacgggtctgacgctcagtgaacgaaaactcacgttaaggattggtcatga
gattatcaaaaggattactttcacctagatccttttaaaatgaagttttaaatcaatctaaagtatatagaacttggtcgacagttaccatctggacccagtcagtgagg
cacctatctcagcactgctctgtctattttcgttcatccatagttgcctgactccccgtcgtgtagataacacggatacggagggcttaccatctggcccagctcaatgatacg
cgagaccacgctcaccggctcagatttatcagcaataaaccagccagcagccgaagtgtcctgcaacttatccgctccatccagtctattaat
tgttgccgggaagctagatagtagttgccagttaatagttgcgaacgttggcaatggttctgctacaggcatcgtgtgtcacgctgtgttatgccttcattcagctcg
gttccaacgatcaaggcgagttacatgatccccatgttgtcaaaaagcgttagctccttcgtcctccgatcgttcagaagtaagttgccgcagtgttatcactcat
ggttatgcgcactgcataattcttactgtcatgccatccgtaagatgctttctgtgactggtgagtactcaaccaagtcttcggggcgaaaactctcaaggatctccgctgtt
ctcttgcccgggtcaataccggatataccgccaccaactgtcacccaactgatcttcagcatcttcctttcaaatattattgaagcatttgtctcatgagcggataacattgaatgttatttagaaaaa
gagatccagttcgatgaacccactcgtgatgtgaatatgttgaatactcatactcttccttttcaaatattattgaagcatttgtctcatgagcggataacatttgaatgttattagaaaaa
taaacaaatagggttccgcgcacattcccgaaagtgccaactgaggtctaagaaaccattattcatgacgtcaaggacgttcacgaggttgtcttgtaagcgaatcacgaggcctttc
gtctcgcgcgtttcggtgatgacggtgaaaacctctgacacatgcagctcgacactgcagctgctcagcatctgaagcgatgccgggagcgagcaagccgtcagggc
gcgtcagcgggtgttggcgggtgcgggtgcggcattgccattcaggtcgggcttaactatgcgccgtcaaactgttggaagggcgatcgtgttgaagtgcaacatatgcggttgaagatcgcacagatgcgtaagg
agaaatccaccgcatcaggccatcagccgccaccagccgcgaaacaaccagccgcgaagctcatgagccgaagtggcgagcgagtcgagacccgaatagatccatagcccaacactgtgct
gcaaggcgattaagttgggtaaccgccaggttttcccagtcacgacgttgtaaaacgacggccagtgaggagatgcgccaacagtccccgg
ccacgggcctgccacctaccccacgccgcaacaaccccacgctgctccggacagctcatgagccgaagtggcgagccgatcttcccatcggtgatgtcggcgatatagggccagcaaccg
cacctgtggccgcggtgatgccgccacgatcgcggccacagcgatgctccaattgttaagacaggatatcagtgtccaagctcgattatagggccagcaaccg
ccacagctgagcctgaagctgatagagtacgagccatagagataaataaagattttattagtctccagaaaaaggggggaa (SEQ ID NO: 26)

SEQUENCE LISTING

<160> NUMBER OF SEQ ID NOS: 26

<210> SEQ ID NO 1
<211> LENGTH: 41
<212> TYPE: PRT
<213> ORGANISM: Homo sapiens

<400> SEQUENCE: 1

Glu Gly Glu Val Ser Ala Asp Glu Glu Gly Phe Glu Asn Leu Trp Ala
1               5                   10                  15

Thr Ala Ser Thr Phe Ile Val Leu Phe Leu Leu Ser Leu Phe Tyr Ser
            20                  25                  30

Thr Thr Val Thr Leu Phe Lys Val Lys
        35                  40

<210> SEQ ID NO 2
<211> LENGTH: 21
<212> TYPE: PRT
<213> ORGANISM: Homo sapiens

<400> SEQUENCE: 2

Leu Leu Leu Leu Phe Trp Leu Gly Trp Leu Gly Met Leu Ala Gly Ala
1               5                   10                  15

Val Val Ile Ile Val
            20

<210> SEQ ID NO 3
<211> LENGTH: 24
<212> TYPE: PRT
<213> ORGANISM: Homo sapiens

<400> SEQUENCE: 3

Lys Ser Leu Gly Ile Leu Gly Ile Leu Leu Gly Val Ala Ala Val Cys
1               5                   10                  15

Thr Ile Ile Ala Leu Ser Val Val
            20

<210> SEQ ID NO 4
<211> LENGTH: 20
<212> TYPE: PRT
<213> ORGANISM: Homo sapiens

<400> SEQUENCE: 4

Ala Leu Ala Trp Glu Leu Leu Gly Ala Ser Val Leu Leu Ile Ala Val
1               5                   10                  15

Arg Trp Leu Val
            20

<210> SEQ ID NO 5
<211> LENGTH: 21
<212> TYPE: PRT
<213> ORGANISM: Homo sapiens

<400> SEQUENCE: 5

Ile Leu Val Leu Leu Ile Leu Ala Val Ile Thr Ile Phe Ala Leu Val
1               5                   10                  15

Cys Val Leu Leu Val
            20

<210> SEQ ID NO 6
<211> LENGTH: 21
<212> TYPE: PRT

<213> ORGANISM: Homo sapiens

<400> SEQUENCE: 6

Phe Phe Thr Trp Phe Met Val Ile Ala Leu Leu Gly Val Trp Thr Ser
1               5                   10                  15
Val Ala Val Val Trp
            20

<210> SEQ ID NO 7
<211> LENGTH: 20
<212> TYPE: PRT
<213> ORGANISM: Homo sapiens

<400> SEQUENCE: 7

Leu Leu Val Ala Val Cys Ala Leu His Leu Gly Val Thr Leu Val Tyr
1               5                   10                  15
Tyr Leu Ala Gly
            20

<210> SEQ ID NO 8
<211> LENGTH: 21
<212> TYPE: PRT
<213> ORGANISM: Homo sapiens

<400> SEQUENCE: 8

Gly Tyr Gly Val Leu Ser Pro Arg Ser Leu Met Pro Gly Ser Leu Glu
1               5                   10                  15
Arg Gly Phe Cys Met
            20

<210> SEQ ID NO 9
<211> LENGTH: 28
<212> TYPE: PRT
<213> ORGANISM: Homo sapiens

<400> SEQUENCE: 9

Lys Leu Leu Leu Gly Ile Gly Ile Leu Val Leu Leu Ile Ile Val Ile
1               5                   10                  15
Leu Gly Val Pro Leu Ile Ile Phe Thr Ile Lys Ala
            20                  25

<210> SEQ ID NO 10
<211> LENGTH: 21
<212> TYPE: PRT
<213> ORGANISM: Homo sapiens

<400> SEQUENCE: 10

Glu Leu Leu Trp Pro Gly Ala Ala Leu Leu Val Leu Leu Gly Val Ala
1               5                   10                  15
Ala Ser Leu Cys Val
            20

<210> SEQ ID NO 11
<211> LENGTH: 24
<212> TYPE: PRT
<213> ORGANISM: Homo sapiens

<400> SEQUENCE: 11

Val Gly Ile Ile Ala Gly Leu Val Leu Leu Gly Ala Val Ile Thr Gly
1               5                   10                  15
Ala Val Val Ala Ala Val Met Trp
            20

<210> SEQ ID NO 12
<211> LENGTH: 17
<212> TYPE: PRT
<213> ORGANISM: Homo sapiens

<400> SEQUENCE: 12

Leu Gly Leu Leu Leu Thr Phe Leu Gly Ile Val Ala Ala Val Leu
1               5                   10                  15

Val

<210> SEQ ID NO 13
<211> LENGTH: 21
<212> TYPE: PRT
<213> ORGANISM: Homo sapiens

<400> SEQUENCE: 13

Leu Tyr Ile Ala Gly Phe Ser Leu Leu Ser Phe Leu Leu Arg Arg
1               5                   10                  15

Leu Val Thr Leu Ile
            20

<210> SEQ ID NO 14
<211> LENGTH: 24
<212> TYPE: PRT
<213> ORGANISM: Homo sapiens

<400> SEQUENCE: 14

Trp Leu Val Leu Leu Ile Ser Met Ala Val Cys Ile Ile Ala Met Ile
1               5                   10                  15

Ile Phe Ser Ser Cys Phe Cys Tyr
            20

<210> SEQ ID NO 15
<211> LENGTH: 21
<212> TYPE: PRT
<213> ORGANISM: Homo sapiens

<400> SEQUENCE: 15

Ile Leu Gly Ile Leu Gly Gly Ile Leu Ala Leu Leu Ile Leu Ile Leu
1               5                   10                  15

Leu Leu Leu Leu Phe
            20

<210> SEQ ID NO 16
<211> LENGTH: 21
<212> TYPE: PRT
<213> ORGANISM: Homo sapiens

<400> SEQUENCE: 16

Ala Val Ile Gly Gly Val Val Ala Val Val Phe Ala Met Leu Cys
1               5                   10                  15

Leu Leu Ile Ile Leu
            20

<210> SEQ ID NO 17
<211> LENGTH: 26
<212> TYPE: PRT
<213> ORGANISM: Homo sapiens

<400> SEQUENCE: 17

Ile Tyr Leu Ile Ile Gly Ile Cys Gly Gly Gly Ser Leu Leu Met Val

```
1               5                   10                  15
Phe Val Ala Leu Leu Val Phe Tyr Ile Thr
            20                  25

<210> SEQ ID NO 18
<211> LENGTH: 21
<212> TYPE: PRT
<213> ORGANISM: Homo sapiens

<400> SEQUENCE: 18

Trp Leu Ile Ile Leu Ala Ser Leu Leu Ala Leu Ala Leu Ile Leu Ala
1               5                   10                  15
Val Cys Ile Ala Val
            20

<210> SEQ ID NO 19
<211> LENGTH: 21
<212> TYPE: PRT
<213> ORGANISM: Homo sapiens

<400> SEQUENCE: 19

Trp Ile Thr Ala Val Leu Pro Thr Val Ile Cys Val Met Val Phe
1               5                   10                  15
Cys Leu Ile Leu Trp
            20

<210> SEQ ID NO 20
<211> LENGTH: 22
<212> TYPE: PRT
<213> ORGANISM: Homo sapiens

<400> SEQUENCE: 20

Ile Ile Thr Ala Glu Gly Ile Ile Leu Leu Phe Cys Ala Val Val Pro
1               5                   10                  15
Gly Thr Leu Leu Leu Phe
            20

<210> SEQ ID NO 21
<211> LENGTH: 25
<212> TYPE: PRT
<213> ORGANISM: Homo sapiens

<400> SEQUENCE: 21

Ala Leu Ile Val Gly Thr Leu Ser Gly Thr Ile Phe Phe Ile Leu Leu
1               5                   10                  15
Ile Ile Phe Leu Ser Trp Ile Ile Leu
            20                  25

<210> SEQ ID NO 22
<211> LENGTH: 21
<212> TYPE: PRT
<213> ORGANISM: Homo sapiens

<400> SEQUENCE: 22

Val Val Val Ala Cys Met Ser Ile Met Ala Leu Leu Leu Leu Leu
1               5                   10                  15
Leu Leu Leu Leu Tyr
            20

<210> SEQ ID NO 23
<211> LENGTH: 687
<212> TYPE: DNA
```

```
<213> ORGANISM: Artificial
<220> FEATURE:
<223> OTHER INFORMATION: Synthetic

<400> SEQUENCE: 23
atgaacccta accaaaagat catcaccatc ggcagcgtgt gcatgaccat aggcatggcc      60
gcactgatcc tggccattgg cgcaatcatc agcatctgga tcagccacag catccagttg     120
ggcaaccaga tcaaatcga gacctgcaat cagtctgtta tcacctacga aaacaacacc     180
tgggtgaacc agacttacgt gaacatcagc ggcagctacc cttacgatgt gcccgactat     240
gccggaggaa gtgaacagaa gttgatcagc gaggaggacc tgaaggtgtt cggcaggtgc     300
gagctggctg ccgccatgaa gaggcacggc ctggataact acgggggta cagcctgggc     360 aactgggtgt gcgccgctaa attcgagagc aacttcaata cgcaggccac caacaggaac     420
accgatggct ctactgacta cggcatcctg caaatcaact ccaggtggtg gtgtaacgac     480
ggcaggaccc ctggaagcag gaacttgtgc aacatcccat gcagcgccct gctgagcagc     540
gacatcaccg ccagcgtgaa ctgcgccaag aagatcgtgt cagacggcaa cggcatgaac     600
gcctgggtgg catggaggaa caggtgcaag gggaccgacg tgcaggcttg gatacgcggc     660
tgtcgacttg gatcaggcag cggttaa                                        687

<210> SEQ ID NO 24
<211> LENGTH: 702
<212> TYPE: DNA
<213> ORGANISM: Artificial
<220> FEATURE:
<223> OTHER INFORMATION: Synthetic

<400> SEQUENCE: 24
atggagaccg acaccctgtt gctgtgggta ctgctcctct gggtgcccgg cagcaccggc      60
gacgggggca gctaccctta cgatgtgccc gactatgccg gaggaagtga acagaagttg     120
atcagcgagg aggacctgaa ggtgttcggc aggtgcgagc tggctgccgc catgaagagg     180
cacggcctgg ataactacag ggggtacagc ctgggcaact gggtgtgcgc cgctaaattc     240
gagagcaact tcaatacgca ggccaccaac aggaacaccg atggctctac tgactacggc     300
atcctgcaaa tcaactccag gtggtggtgt aacgacggca ggacccctgg aagcaggaac     360
ttgtgcaaca tcccatgcag cgccctgctg agcagcgaca tcaccgccag cgtgaactgc     420
gccaagaaga tcgtgtcaga cggcaacggc atgaacgcct gggtggcatg gaggaacagg     480
tgcaagggga ccgacgtgca ggcttggata cgcggctgtc gacttggatc aggcagcggt     540
tcagggtcag gctcagccgt gggccaggac acccaagagg tgatcgtggt gcctcatagc     600
ctccctttca aggttgtggt gatctcagct atcctggcac tggtcgtgct gaccatcatc     660
agcctgataa tactgattat gttgtggcag aagaaaccta gg                       702

<210> SEQ ID NO 25
<211> LENGTH: 8348
<212> TYPE: DNA
<213> ORGANISM: Artificial
<220> FEATURE:
<223> OTHER INFORMATION: Synthetic

<400> SEQUENCE: 25
tgaaagaccc cacctgtagg tttggcaagc tagcttaagt aacgccattt tgcaaggcat      60
ggaaaataca taactgagaa tagagaagtt cagatcaagg ttaggaacag agagacagca     120
gaatatgggc caaacaggat atctgtggta agcagttcct gccccggctc agggccaaga     180
```

```
acagatggtc cccagatgcg gtcccgccct cagcagtttc tagagaacca tcagatgttt    240
ccagggtgcc ccaaggacct gaaatgaccc tgtgccttat ttgaactaac caatcagttc    300
gcttctcgct tctgttcgcg cgcttctgct ccccgagctc aataaaagag cccacaaccc    360
ctcactcggc gcgccagtcc tccgatagac tgcgtcgccc gggtacccgt attcccaata    420
aagcctcttg ctgtttgcat ccgaatcgtg gactcgctga tccttgggag gtctcctca     480 gattgattga ctgcccacct cggggggtctt tcatttggag gttccaccga gatttggaga    540
cccctgccca gggaccaccg accccccgc cgggaggtaa gctggccagc ggtcgtttcg     600
tgtctgtctc tgtctttgtg cgtgtttgtg ccggcatcta atgtttgcgc ctgcgtctgt    660
actagttagc taactagctc tgtatctggc ggacccgtgg tggaactgac gagttctgaa    720
cacccggccg caaccctggg agacgtccca gggactttgg gggccgtttt tgtggcccga    780
cctgaggaag ggagtcgatg tggaatccga ccccgtcagg atatgtggtt ctggtaggag    840
acgagaacct aaaacagttc ccgcctccgt ctgaatttttt gctttcggtt tggaaccgaa    900
gccgcgcgtc ttgtctgctg cagcgctgca gcatcgttct gtgttgtctc tgtctgactg    960
tgtttctgta tttgtctgaa aattagggcc agactgttac cactccctta agtttgacct   1020
taggtcactg gaaagatgtc gagcggatcg ctcacaacca gtcggtagat gtcaagaaga   1080
gacgttgggt taccttctgc tctgcagaat ggccaacctt taacgtcgga tggccgcgag   1140
acggcacctt taaccgagac ctcatcaccc aggttaagat caaggtcttt tcacctggcc   1200
cgcatggaca cccagaccag gtcccctaca tcgtgacctg ggaagccttg gcttttgacc   1260
cccctccctg ggtcaagccc tttgtacacc ctaagcctcc gcctcctctt cctccatccg   1320
ccccgtctct ccccctttgaa cctcctcgtt cgacccccgcc tcgatcctcc ctttatccag   1380
ccctcactcc ttctctaggc gccggaatta gatctgccat gaaccctaac caaaagatca   1440
tcaccatcgg cagcgtgtgc atgaccatag gcatggccgc actgatcctg gccattggcg   1500
caatcatcag catctggatc agccacagca tccagttggg caaccagaat caaatcgaga   1560
cctgcaatca gtctgttatc acctacgaga acaacacctg ggtgaaccag acttacgtga   1620
acatcagcgg cagctaccct tacgatgtgc ccgactatgc cggaggaagt gaacagaagt   1680
tgatcagcga ggaggacctg aaggtgttcg gcaggtgcga gctggctgcc gccatgaaga   1740
ggcacggcct ggataactac aggggtaca gcctgggcaa ctgggtgtgc gccgctaaat   1800
tcgagagcaa cttcaatacg caggccacca acaggaacac cgatggctct actgactacg   1860
gcatcctgca aatcaactcc aggtggtggt gtaacgacgg caggaccct ggaagcagga    1920 acttgtgcaa catcccatgc agcgccctgc tgagcagcga catcaccgcc agcgtgaact   1980
gcgccaagaa gatcgtgtca gacggcaacg gcatgaacgc ctgggtggca tggaggaaca   2040
ggtgcaaggg gaccgacgtg caggcttgga tacgcggctg tcgacttgga tcaggcagcg   2100
gttaactcga ggttaacgaa ttctaccggg tagggaggg gcttttccca aggcagtctg    2160
gagcatgcgc tttagcagcc ccgctgggca cttggcgcta cacaagtggc ctctggcctc   2220
gcacacattc cacatccacc ggtaggcgcc aaccggctcc gttctttggt ggccccttcg   2280
cgccaccttc tactcctccc ctagtcagga agttcccccc cgccccgcag ctcgcgtcgt    2340
gcaggacgtg acaaatggaa gtagcacgtc tcactagtct cgtgcagatg gacagcaccg   2400
ctgagcaatg gaagcgggta ggcctttggg gcagcggcca atagcagctt tgctccttcg   2460
ctttctgggc tcagaggctg ggaaggggtg ggtccggggg cgggctcagg ggcgggctca   2520
```

```
ggggcggggc gggcgcccga aggtcctccg gaggcccggc attctgcacg cttcaaaagc    2580
gcacgtctgc cgcgctgttc tcctcttcct catctccggg cctttcgacc tgcagcccaa    2640
gcttaccatg accgagtaca agcccacggt gcgcctcgcc acccgcgacg acgtccccag    2700
ggccgtacgc accctcgccg ccgcgttcgc cgactacccc gccacgcgcc acaccgtcga    2760
tccggaccgc cacatcgagc gggtcaccga gctgcaagaa ctcttcctca cgcgcgtcgg    2820
gctcgacatc ggcaaggtgt gggtcgcgga cgacggcgcc gcggtggcgg tctgaccac     2880 gccggagagc gtcgaagcgg gggcggtgtt cgccgagatc ggcccgcgca tggccgagtt    2940
gagcggttcc cggctggccg cgcagcaaca gatggaaggc ctcctggcgc cgcaccggcc    3000
caaggagccc gcgtggttcc tggccaccgt cggcgtctcg cccgaccacc agggcaaggg    3060
tctgggcagc gccgtcgtgc tccccggagt ggaggcggcc gagcgcgccg gggtgcccgc    3120
cttcctggag acctccgcgc cccgcaacct ccccttctac gagcggctcg gcttcaccgt    3180
caccgccgac gtcgaggtgc ccgaaggacc gcgcacctgg tgcatgaccc gcaagcccgg    3240
tgcctgacgc ccgccccacg acccgcagcg cccgaccgaa aggagcgcac gaccccatgc    3300
atccaattcc gcccccccc cctaacgtta ctggccgaag ccgcttggaa taaggccggt     3360
gtgcgtttgt ctatatgtta ttttccacca tattgccgtc ttttggcaat gtgagggccc    3420
ggaaacctgg ccctgtcttc ttgacgagca ttcctagggg tctttcccct ctcgccaaag    3480
gaatgcaagg tctgttgaat gtcgtgaagg aagcagttcc tctggaagct tcttgaagac    3540
aaacaacgtc tgtagcgacc ctttgcaggc agcggaaccc cccacctggc gacaggtgcc    3600
tctgcggcca aaagccacgt gtataagata cacctgcaaa ggcggcacaa ccccagtgcc    3660
acgttgtgag ttggatagtt gtggaaagag tcaaatggct ctcctcaagc gtattcaaca    3720
aggggctgaa ggatgcccag aaggtacccc attgtatggg atctgatctg gggcctcggt    3780
gcacatgctt tacatgtgtt tagtcgaggt taaaaaaacg tctaggcccc ccgaaccacg    3840
gggacgtggt tttcctttga aaaacacgat gataatatgg ccacaaccat ggtgagcaag    3900
ggcgaggagc tgttcaccgg ggtggtgccc atcctggtcg agctggacgg cgacgtaaac    3960
ggccacaagt tcagcgtgtc tggcgagggc gagggcgatg ccacctacgg caagctgacc    4020
ctgaagttca tctgcaccac cggcaagctg cccgtgccct ggcccaccct cgtgaccacc    4080
ctgacctacg gcgtgcagtg cttcagccgc taccccgacc acatgaagca gcacgacttc    4140
ttcaagtccg ccatgcccga aggctacgtc caggagcgca ccatcttctt caaggacgac    4200
ggcaactaca agacccgcgc cgaggtgaag ttcgagggcg acaccctggt gaaccgcatc    4260
gagctgaagg gcatcgactt caaggaggac ggcaacatcc tggggcacaa gctggagtac    4320
aactacaaca gccacaacgt ctatatcatg gccgacaagc agaagaacgg catcaaggcg    4380
aacttcaaga tccgccacaa catcgaggac ggcagcgtgc agctcgccga ccactaccag    4440
cagaacaccc ccatcggcga cggccccgtg ctgctgcccg acaaccacta cctgagcacc    4500
cagtccgccc tgagcaaaga ccccaacgag aagcgcgatc acatggtcct gctggagttc    4560
gtgaccgccg ccgggatcac tctcggcatg gacgagctgt acaagtaatg aattaattaa    4620
gaattatcaa gcttatcgat accgtcgacc tgcagccaag cttatcgata aaataaaaga    4680
ttttatttag tctccagaaa aaggggggaa tgaaagaccc cacctgtagg tttggcaagc    4740
tagcttaagt aacgccattt tgcaaggcat ggaaaataca taactgagaa tagagaagtt    4800
cagatcaagg ttaggaacag agagacagca gaatatgggc caaacaggat atctgtggta    4860
agcagttcct gccccggctc agggccaaga acagatggtc cccagatgcg gtcccgccct    4920
```

```
cagcagtttc tagagaacca tcagatgttt ccagggtgcc ccaaggacct gaaatgaccc    4980
tgtgccttat ttgaactaac caatcagttc gcttctcgct tctgttcgcg cgcttctgct    5040
ccccgagctc aataaaagag cccacaaccc ctcactcggc gcgccagtcc tccgatagac    5100
tgcgtcgccc gggtacccgt gtatccaata aaccctcttg cagttgcatc cgacttgtgg    5160
tctcgctgtt ccttgggagg gtctcctctg agtgattgac tacccgtcag cgggggtctt    5220
tcatgggtaa cagtttcttg aagttggaga acaacattct gagggtagga gtcgaatatt    5280
aagtaatcct gactcaatta gccactgttt tgaatccaca tactccaata ctcctgaaat    5340
agttcattat ggacagcgca gaagagctgg ggagaattaa ttcgtaatca tggtcatagc    5400
tgtttcctgt gtgaaattgt tatccgctca caattccaca acatacga gccggaagca     5460 taaagtgtaa agcctggggt gcctaatgag tgagctaact cacattaatt gcgttgcgct    5520
cactgcccgc tttccagtcg ggaaacctgt cgtgccagct gcattaatga atcggccaac    5580
gcgcggggag aggcggtttg cgtattgggc gctcttccgc ttcctcgctc actgactcgc    5640
tgcgctcggt cgttcggctg cggcgagcgg tatcagctca ctcaaaggcg gtaatacggt    5700
tatccacaga atcaggggat aacgcaggaa agaacatgtg agcaaaaggc cagcaaaagg    5760
ccaggaaccg taaaaaggcc gcgttgctgg cgtttttcca taggctccgc cccctgacg    5820 agcatcacaa aaatcgacgc tcaagtcaga ggtggcgaaa cccgacagga ctataaagat    5880
accaggcgtt ccccctgga agctccctcg tgcgctctcc tgttccgacc ctgccgctta    5940
ccggatacct gtccgccttt ctcccttcgg aagcgtggc gctttctcat agctcacgct    6000
gtaggtatct cagttcggtg taggtcgttc gctccaagct gggctgtgtg cacgaacccc    6060
ccgttcagcc cgaccgctgc gccttatccg gtaactatcg tcttgagtcc aacccggtaa    6120
gacacgactt atcgccactg gcagcagcca ctggtaacag gattagcaga gcgaggtatg    6180
taggcggtgc tacagagttc ttgaagtggt ggcctaacta cggctacact agaaggacag    6240
tatttggtat ctgcgctctg ctgaagccag ttaccttcgg aaaaagagtt ggtagctctt    6300
gatccggcaa acaaaccacc gctggtagcg gtggttttttt tgtttgcaag cagcagatta    6360
cgcgcagaaa aaaggatct caagaagatc ctttgatctt ttctacgggg tctgacgctc    6420
agtggaacga aaactcacgt taagggattt tggtcatgag attatcaaaa aggatcttca    6480
cctagatcct tttaaattaa aaatgaagtt ttaaatcaat ctaaagtata tatgagtaaa    6540
cttggtctga cagttaccaa tgcttaatca gtgaggcacc tatctcagcg atctgtctat    6600
ttcgttcatc catagttgcc tgactccccg tcgtgtagat aactacgata cgggagggct    6660
taccatctgg ccccagtgct gcaatgatac cgcgagaccc acgctcaccg gctccagatt    6720
tatcagcaat aaaccagcca gccggaaggg ccgagcgcag aagtggtcct gcaactttat    6780
ccgcctccat ccagtctatt aattgttgcc gggaagctag agtaagtagt tcgccagtta    6840
atagtttgcg caacgttgtt gccattgcta caggcatcgt ggtgtcacgc tcgtcgtttg    6900
gtatggcttc attcagctcc ggttcccaac gatcaaggcg agttacatga tcccccatgt    6960
tgtgcaaaaa agcggttagc tccttcggtc ctccgatcgt tgtcagaagt aagttggccg    7020
cagtgttatc actcatggtt atggcagcac tgcataattc tcttactgtc atgccatccg    7080
taagatgctt ttctgtgact ggtgagtact caaccaagtc attctgagaa tagtgtatgc    7140
ggcgaccgag ttgctcttgc ccggcgtcaa tacgggataa taccgcgcca catagcagaa    7200
ctttaaaagt gctcatcatt ggaaaacgtt cttcggggcg aaaactctca aggatcttac    7260
```

| | |
|---|---|
| cgctgttgag atccagttcg atgtaaccca ctcgtgcacc caactgatct tcagcatctt | 7320 |
| ttactttcac cagcgtttct gggtgagcaa aaacaggaag gcaaaatgcc gcaaaaaagg | 7380 |
| gaataagggc gacacggaaa tgttgaatac tcatactctt ccttttttcaa tattattgaa | 7440 |
| gcatttatca gggttattgt ctcatgagcg gatacatatt tgaatgtatt tagaaaaata | 7500 |
| aacaaatagg ggttccgcgc acatttcccc gaaaagtgcc acctgacgtc taagaaacca | 7560 |
| ttattatcat gacattaacc tataaaaata ggcgtatcac gaggcccttt cgtctcgcgc | 7620 |
| gtttcggtga tgacggtgaa aacctctgac acatgcagct cccggagacg gtcacagctt | 7680 |
| gtctgtaagc ggatgccggg agcagacaag cccgtcaggg cgcgtcagcg ggtgttggcg | 7740 |
| ggtgtcgggg ctggcttaac tatgcggcat cagagcagat tgtactgaga gtgcaccata | 7800 |
| tgcggtgtga ataccgcac agatgcgtaa ggagaaaata ccgcatcagg cgccattcgc | 7860 |
| cattcaggct gcgcaactgt tgggaagggc gatcggtgcg ggcctcttcg ctattacgcc | 7920 |
| agctggcgaa aggggggatgt gctgcaaggc gattaagttg ggtaacgcca gggttttccc | 7980 |
| agtcacgacg ttgtaaaacg acggcgcaag gaatggtgca tgcaaggaga tggcgcccaa | 8040 |
| cagtccccccg gccacggggc ctgccaccat acccacgccg aaacaagcgc tcatgagccc | 8100 |
| gaagtggcga gcccgatctt ccccatcggt gatgtcggcg atataggcgc cagcaaccgc | 8160 |
| acctgtggcg ccggtgatgc cggccacgat gcgtccggcg tagaggcgat tagtccaatt | 8220 |
| tgttaaagac aggatatcag tggtccaggc tctagttttg actcaacaat atcaccagct | 8280 |
| gaagcctata gagtacgagc catagataaa ataaaagatt ttatttagtc tccagaaaaa | 8340 |
| gggggggaa | 8348 |

<210> SEQ ID NO 26
<211> LENGTH: 8366
<212> TYPE: DNA
<213> ORGANISM: Artificial
<220> FEATURE:
<223> OTHER INFORMATION: Synthetic

<400> SEQUENCE: 26

| | |
|---|---|
| tgaaagaccc cacctgtagg tttggcaagc tagcttaagt aacgccattt tgcaaggcat | 60 |
| ggaaaataca taactgagaa tagagaagtt cagatcaagg ttaggaacag agagacagca | 120 |
| gaatatgggc caaacaggat atctgtggta agcagttcct gccccggctc agggccaaga | 180 |
| acagatggtc cccagatgcg gtcccgccct cagcagtttc tagagaacca tcagatgttt | 240 |
| ccagggtgcc ccaaggacct gaaatgaccc tgtgccttat ttgaactaac caatcagttc | 300 |
| gcttctcgct tctgttcgcg cgcttctgct ccccgagctc aataaaagag cccacaaccc | 360 |
| ctcactcggc gcgccagtcc tccgatagac tgcgtcgccc gggtacccgt attcccaata | 420 |
| aagcctcttg ctgtttgcat ccgaatcgtg gactcgctga tccttgggag ggtctcctca | 480 |
| gattgattga ctgcccacct cggggggtctt tcatttggag gttccaccga gatttggaga | 540 |
| ccccctgccca gggaccaccg acccccccgc cgggaggtaa gctggccagc ggtcgtttcg | 600 |
| tgtctgtctc tgtctttgtg cgtgtttgtg ccggcatcta atgtttgcgc ctgcgtctgt | 660 |
| actagttagc taactagctc tgtatctggc ggacccgtgg tggaactgac gagttctgaa | 720 |
| cacccggccg caaccctggg agacgtccca gggactttgg gggccgtttt tgtggcccga | 780 |
| cctgaggaag gggtcgatg tggaatccga ccccgtcagg atatgtggtt ctggtaggag | 840 |
| acgagaacct aaaacagttc ccgcctccgt ctgaattttt gctttcggtt tggaaccgaa | 900 |
| gccgcgcgtc ttgtctgctg cagcgctgca gcatcgttct gtgttgtctc tgtctgactg | 960 |

```
tgtttctgta tttgtctgaa aattagggcc agactgttac cactcccttta agtttgacct   1020
taggtcactg gaaagatgtc gagcggatcg ctcacaacca gtcggtagat gtcaagaaga   1080
gacgttgggt taccttctgc tctgcagaat ggccaacctt taacgtcgga tggccgcgag   1140
acggcacctt taaccgagac ctcatcaccc aggttaagat caaggtcttt tcacctggcc   1200
cgcatggaca cccagaccag gtcccctaca tcgtgacctg ggaagccttg gcttttgacc   1260
cccctccctg ggtcaagccc tttgtacacc ctaagcctcc gcctcctctt cctccatccg   1320
ccccgtctct ccccccttgaa cctcctcgtt cgaccccgcc tcgatcctcc ctttatccag   1380
ccctcactcc ttctctaggc gccggaatta gatctgccat ggagaccgac accctgttgc   1440
tgtgggtact gctcctctgg gtgcccggca gcaccggcga cggggggcagc taccccttacg   1500
atgtgcccga ctatgccgga ggaagtgaac agaagttgat cagcgaggag gacctgaagg   1560
tgttcggcag gtgcgagctg gctgccgcca tgaagaggca cggcctggat aactacaggg   1620
ggtacagcct gggcaactgg gtgtgcgccg ctaaattcga gagcaacttc aatacgcagg   1680
ccaccaacag gaacaccgat ggctctactg actacggcat cctgcaaatc aactccaggt   1740
ggtggtgtaa cgacggcagg accccctggaa gcaggaactt gtgcaacatc ccatgcagcg   1800
ccctgctgag cagcgacatc accgccagcg tgaactgcgc caagaagatc gtgtcagacg   1860
gcaacggcat gaacgcctgg gtggcatgga ggaacaggtg caagggggacc gacgtgcagg   1920
cttggatacg cggctgtcga cttggatcag gcagcggttc agggtcaggc tcagccgtgg   1980
gccaggacac ccaagaggtg atcgtggtgc ctcatagcct cccttttcaag gttgtggtga   2040
tctcagctat cctggcactg gtcgtgctga ccatcatcag cctgataata ctgattatgt   2100
tgtggcagaa gaaacctagg taactcgagg ttaacgaatt ctaccgggta ggggaggcgc   2160
ttttcccaag gcagtctgga gcatgcgctt tagcagcccc gctgggcact ggcgctaca   2220
caagtggcct ctggcctcgc acacattcca catccaccgg taggcgccaa ccggctccgt   2280
tctttggtgg ccccccttcgcg ccaccttcta ctcctcccct agtcaggaag ttcccccccg   2340
ccccgcagct cgcgtcgtgc aggacgtgac aaatggaagt agcacgtctc actagtctcg   2400
tgcagatgga cagcaccgct gagcaatgga agcgggtagg cctttggggc agcggccaat   2460
agcagctttg ctccttcgct ttctgggctc agaggctggg aaggggtggg tccggggcg   2520
ggctcagggg cgggctcagg ggcggggcgg gcgcccgaag gtcctccgga ggcccggcat   2580
tctgcacgct tcaaaagcgc acgtctgccg cgctgttctc ctcttcctca tctccgggcc   2640
tttcgacctg cagcccaagc ttaccatgac cgagtacaag cccacggtgc gcctcgccac   2700
ccgcgacgac gtccccaggg ccgtacgcac cctcgccgcc gcgttcgccg actaccccgc   2760
cacgcgccac accgtcgatc cggaccgcca catcgagcgg gtcaccgagc tgcaagaact   2820
cttcctcacg cgcgtcgggc tcgacatcgg caaggtgtgg gtcgcggacg acggcgccgc   2880
ggtggcggtc tggaccacgc cggagagcgt cgaagcgggg gcggtgttcg ccgagatcgg   2940
cccgcgcatg gccgagttga gcggttcccg gctggccgcg cagcaacaga tggaaggcct   3000
cctggcgccg caccggccca aggagcccgc gtggttcctg gccaccgtcg gcgtctcgcc   3060
cgaccaccag ggcaagggtc tgggcagcgc cgtcgtgctc cccggagtgg aggcggccga   3120
gcgcgccggg gtgcccgcct tcctggagac ctccgcgccc cgcaacctcc ccttctacga   3180
gcggctcggc ttcaccgtca ccgccgacgt cgaggtgccc gaaggaccgc gcacctggtg   3240
catgacccgc aagcccggtg cctgacgccc gccccacgac ccgcagcgcc cgaccgaaag   3300
```

```
gagcgcacga ccccatgcat ccaattccgc cccccccccc taacgttact ggccgaagcc    3360
gcttggaata aggccggtgt gcgtttgtct atatgttatt ttccaccata ttgccgtctt    3420
ttggcaatgt gagggcccgg aaacctggcc ctgtcttctt gacgagcatt cctagggtc     3480 tttcccctct cgccaaagga atgcaaggtc tgttgaatgt cgtgaaggaa gcagttcctc    3540
tggaagcttc ttgaagacaa acaacgtctg tagcgaccct ttgcaggcag cggaaccccc    3600
cacctggcga caggtgcctc tgcggccaaa agccacgtgt ataagataca cctgcaaagg    3660
cggcacaacc ccagtgccac gttgtgagtt ggatagttgt ggaaagagtc aaatggctct    3720
cctcaagcgt attcaacaag gggctgaagg atgcccagaa ggtaccccat tgtatgggat    3780
ctgatctggg gcctcggtgc acatgcttta catgtgttta gtcgaggtta aaaaaacgtc    3840
taggcccccc gaaccacggg gacgtggttt cctttgaaa aacacgatga taatatggcc     3900
acaaccatgg tgagcaaggg cgaggagctg ttcaccgggg tggtgcccat cctggtcgag    3960
ctggacggcg acgtaaacgg ccacaagttc agcgtgtctg gcgagggcga gggcgatgcc    4020
acctacggca agctgaccct gaagttcatc tgcaccaccg gcaagctgcc cgtgccctgg    4080
cccaccctcg tgaccaccct gacctacggc gtgcagtgct tcagccgcta ccccgaccac    4140
atgaagcagc acgacttctt caagtccgcc atgcccgaag gctacgtcca ggagcgcacc    4200
atcttcttca aggacgacgg caactacaag acccgcgccg aggtgaagtt cgagggcgac    4260
accctggtga accgcatcga gctgaagggc atcgacttca aggaggacgg caacatcctg    4320
gggcacaagc tggagtacaa ctacaacagc cacaacgtct atatcatggc cgacaagcag    4380
aagaacggca tcaaggcgaa cttcaagatc cgccacaaca tcgaggacgg cagcgtgcag    4440
ctcgccgacc actaccagca gaacaccccc atcggcgacg gccccgtgct gctgcccgac    4500
aaccactacc tgagcaccca gtccgccctg agcaaagacc ccaacgagaa gcgcgatcac    4560
atggtcctgc tggagttcgt gaccgccgcc gggatcactc tcggcatgga cgagctgtac    4620
aagtaatgaa ttaattaaga attatcaagc ttatcgatac cgtcgacctg cagccaagct    4680
tatcgataaa ataaaagatt ttatttagtc tccagaaaaa ggggggaatg aaagacccca    4740
cctgtaggtt tggcaagcta gcttaagtaa cgccattttg caaggcatgg aaaatacata    4800
actgagaata gagaagttca gatcaaggtt aggaacagag agacagcaga atatgggcca    4860
aacaggatat ctgtggtaag cagttcctgc cccggctcag ggccaagaac agatggtccc    4920
cagatgcggt cccgccctca gcagtttcta gagaaccatc agatgtttcc agggtgcccc    4980
aaggacctga atgacctg tgccttattt gaactaacca atcagttcgc ttctcgcttc       5040
tgttcgcgcg cttctgctcc ccgagctcaa taaaagagcc cacaacccct cactcggcgc    5100
gccagtcctc cgatagactg cgtcgcccgg gtaccgtgt atccaataaa ccctcttgca     5160
gttgcatccg acttgtggtc tcgctgttcc ttgggagggt ctcctctgag tgattgacta    5220
cccgtcagcg ggggtctttc atgggtaaca gtttcttgaa gttggagaac aacattctga    5280
gggtaggagt cgaatattaa gtaatcctga ctcaattagc cactgttttg aatccacata    5340
ctccaatact cctgaaatag ttcattatgg acagcgcaga agagctgggg agaattaatt    5400
cgtaatcatg gtcatagctg tttcctgtgt gaaattgtta tccgctcaca attccacaca    5460
acatacgagc cggaagcata agtgtaaag cctggggtgc ctaatgagtg agctaactca      5520
cattaattgc gttgcgctca ctgcccgctt tccagtcggg aaacctgtcg tgccagctgc    5580
attaatgaat cggccaacgc gcggggagag gcggtttgcg tattgggcgc tcttccgctt    5640
cctcgctcac tgactcgctg cgctcggtcg ttcggctgcg gcgagcggta tcagctcact    5700
```

```
caaaggcggt aatacggtta tccacagaat caggggataa cgcaggaaag aacatgtgag   5760
caaaaggcca gcaaaaggcc aggaaccgta aaaaggccgc gttgctggcg ttttcccata   5820
ggctccgccc ccctgacgag catcacaaaa atcgacgctc aagtcagagg tggcgaaacc   5880
cgacaggact ataaagatac caggcgtttc ccctggaag ctccctcgtg cgctctcctg    5940
ttccgaccct gccgcttacc ggatacctgt ccgcctttct cccttcggga agcgtggcgc   6000
tttctcatag ctcacgctgt aggtatctca gttcggtgta ggtcgttcgc tccaagctgg   6060
gctgtgtgca cgaaccccc gttcagcccg accgctgcgc cttatccggt aactatcgtc    6120
ttgagtccaa cccggtaaga cacgacttat cgccactggc agcagccact ggtaacagga   6180
ttagcagagc gaggtatgta ggcggtgcta cagagttctt gaagtggtgg cctaactacg   6240
gctacactag aaggacagta tttggtatct gcgctctgct gaagccagtt accttcggaa   6300
aaagagttgg tagctcttga tccggcaaac aaaccaccgc tggtagcggt ggtttttttg   6360
tttgcaagca gcagattacg cgcagaaaaa aaggatctca agaagatcct ttgatctttt   6420
ctacggggtc tgacgctcag tggaacgaaa actcacgtta agggattttg gtcatgagat   6480
tatcaaaaag gatcttcacc tagatccttt taaattaaaa atgaagtttt aaatcaatct   6540
aaagtatata tgagtaaact tggtctgaca gttaccaatg cttaatcagt gaggcaccta   6600
tctcagcgat ctgtctattt cgttcatcca tagttgcctg actccccgtc gtgtagataa   6660
ctacgatacg ggagggctta ccatctggcc ccagtgctgc aatgataccg cgagacccac   6720
gctcaccggc tccagattta tcagcaataa accagccagc cggaagggcc gagcgcagaa   6780
gtggtcctgc aactttatcc gcctccatcc agtctattaa ttgttgccgg gaagctagag   6840
taagtagttc gccagttaat agtttgcgca acgttgttgc cattgctaca ggcatcgtgg   6900
tgtcacgctc gtcgtttggt atggcttcat tcagctccgg ttcccaacga tcaaggcgag   6960
ttacatgatc ccccatgttg tgcaaaaaag cggttagctc cttcggtcct ccgatcgttg   7020
tcagaagtaa gttggccgca gtgttatcac tcatggttat ggcagcactg cataattctc   7080
ttactgtcat gccatccgta agatgctttt ctgtgactgg tgagtactca accaagtcat   7140
tctgagaata gtgtatgcgg cgaccgagtt gctcttgccc ggcgtcaata cgggataata   7200
ccgcgccaca tagcagaact ttaaaagtgc tcatcattgg aaaacgttct cggggcgaa    7260 aactctcaag gatcttaccg ctgttgagat ccagttcgat gtaacccact cgtgcaccca   7320
actgatcttc agcatctttt actttcacca gcgtttctgg gtgagcaaaa acaggaaggc   7380
aaaatgccgc aaaaaaggga ataagggcga cacggaaatg ttgaatactc atactcttcc   7440
tttttcaata ttattgaagc atttatcagg gttattgtct catgagcgga tacatatttg   7500
aatgtattta gaaaaataaa caaatagggg ttccgcgcac atttccccga aaagtgccac   7560
ctgacgtcta agaaaccatt attatcatga cattaaccta taaaaatagg cgtatcacga   7620
ggccctttcg tctcgcgcgt ttcggtgatg acggtgaaaa cctctgacac atgcagctcc   7680
cggagacggt cacagcttgt ctgtaagcgg atgccgggag cagacaagcc cgtcagggcg   7740
cgtcagcggg tgttggcggg tgtcggggct ggcttaacta tgcggcatca gagcagattg   7800
tactgagagt gcaccatatg cggtgtgaaa taccgcacag atgcgtaagg agaaaatacc   7860
gcatcaggcg ccattcgcca ttcaggctgc gcaactgttg ggaagggcga tcggtgcggg   7920
cctcttcgct attacgccag ctggcgaaag gggatgtgc tgcaaggcga ttaagttggg    7980
taacgccagg gttttcccag tcacgacgtt gtaaaacgac ggcgcaagga atggtgcatg   8040
```

```
caaggagatg gcgcccaaca gtcccccggc cacggggcct gccaccatac ccacgccgaa    8100
acaagcgctc atgagcccga agtggcgagc ccgatcttcc ccatcggtga tgtcggcgat    8160
ataggcgcca gcaaccgcac ctgtggcgcc ggtgatgccg gccacgatgc gtccggcgta    8220
gaggcgatta gtccaatttg ttaaagacag gatatcagtg gtccaggctc tagttttgac    8280
tcaacaatat caccagctga agcctataga gtacgagcca tagataaaat aaaagatttt    8340
atttagtctc cagaaaaagg ggggaa                                         8366
```

FUNCTIONAL CHARACTERIZATION OF IMMUNE REPERTOIRES

CROSS REFERENCE TO RELATED APPLICATIONS

This application claims the benefit of U.S. Provisional Application No. 62/406,115, filed on Oct. 10, 2016, which is hereby incorporated by reference in its entirety.

REFERENCE TO ELECTRONIC SEQUENCE LISTING

The present application is being filed along with an Sequence Listing in electronic format. The Electronic Sequence Listing is provided as a file entitled CALTE125ASEQLIST.TXT, created on Oct. 9, 2017 and last modified on Oct. 10, 2017, which is 30,259 bytes in size. The information in the electronic format of the Electronic Sequence Listing is incorporated herein by reference in its entirety

BACKGROUND

Field

The present disclosure is related to elucidation of immunological repertoires. In some embodiments, the present disclosure is related to elucidation of repertoires of functional immune cell receptors and antigens by high-throughput sequencing.

The immune system of humans and other mammals records its previous encounters with pathogens and non-self-antigens in the form of millions of memory T and B cells (which comprise an adaptive immune system) that can persists for a lifetime and provide for prophylaxis and rapid response against future challenges with pathogens and non-self-antigens. Immunological memory is encoded in the form of millions of distinct antigen-specific B cell receptors (BCRs) and T cell receptors (TCRs), collectively referred to as an "immunological repertoire."

SUMMARY

In some embodiments, a method of isolating individual components of functional receptor-antigen synapses comprised by an immunological repertoire is provided. In some embodiments, the method comprises contacting a first population of cells expressing an antigen on the cell surface with a second population of cells expressing an immune cell receptor on the cell surface, so that the cells of the first population and cells of the second population bind to each other to form doublets of cells via formation of antigen-immune cell receptor pairs. The method can further comprise isolating the doublets of cells, in which each doublet comprises one cell from the first population and one cell from the second population. The method can further comprise determining the sequence of the antigen-immune cell receptor pairs, thus isolating individual components of functional receptor-antigen synapses comprised by an immunological repertoire. In some embodiments of the method, the first population of cells expresses a heterogeneous repertoire of antigens. In some embodiments of the method, the second population of cells expresses a heterogeneous repertoire of immune cell receptors.

In some embodiments, a method of sequencing mRNAs of a doublet of cells is provided. The method can comprise isolating a doublet comprising a first cell and a second cell that form an immunological synapse between an antigen expressed on the first cell surface and an immune cell receptor expressed on the second cell surface. The method can comprise contacting mRNA from the first and second cells of the isolated doublet, on which an mRNA from the first cell encodes the antigen and an mRNA from the second cell encodes the immune cell receptor. The method can comprise sequencing the mRNAs from the first and second cells. In some embodiments, the method of sequencing mRNAs further comprises contacting the mRNA of the isolated doublet with a solid phase comprising a first oligonucleotide comprising a first sequence complementary to the mRNA encoding the antigen and a second oligonucleotide comprising a second sequence complementary to the mRNA encoding the immune cell receptor. The method can comprise sequencing mRNAs that hybridize to the solid phase. In some embodiments of the method of sequencing mRNAs: (a) the first sequence is complementary to coding sequence for the antigen, (b) the second sequence is complementary to coding sequence for the immune cell receptor, or both (a) and (b). In some embodiments, the method of sequencing mRNAs further comprising forming the doublet by co-incubating a first population of cells each expressing an antigen, wherein the antigen of any two cells of the first population can be the same or different, and a second population of cells each expressing an immune cell receptor that binds the antigen, wherein the immune cell receptor of any two cells of the second population can be the same or different, thereby forming a population of doublets comprising the doublet. In some embodiments of the method of sequencing mRNAs, the first oligonucleotide, the second oligonucleotide, or both further comprise an oligo dT sequence. In some embodiments of the method of sequencing mRNAs, the solid phase comprises beads. In some embodiments of the method of sequencing mRNAs, the sequencing is performed by emulsion-based bead sequencing. In some embodiments of the method of sequencing mRNAs, the cells of the second population are lymphocytes. In some embodiments of the method of sequencing mRNAs, the lymphocyte is selected from the group consisting of B cells, CD4 T cells, CD8 T cells, Gamma-Delta T cells, NK T cells, and any hematopoietically-derived cells. In some embodiments, the method of sequencing mRNAs further comprising isolating additional doublets from the population of doublets and sequencing mRNAs encoding the antigen and the immune cell receptor from the additional doublets, thereby obtaining sequence information of a repertoire of antigens and a repertoire of immune cell receptors that bind each other. In some embodiments of the method of sequencing mRNAs, the first population of cells expresses a heterogeneous repertoire of antigens. In some embodiments of the method of sequencing mRNAs, the second population of cells expresses a heterogeneous repertoire of immune cell receptors.

In some embodiments, a kit for obtaining sequence information of an antigen and an immune cell receptor that binds to the antigen is provided. In some the kit comprises a vector for expressing an antigen on the surface of a cell, the vector comprising a sequence encoding a type II transmembrane sequence, an insertion site configured to contain a sequence encoding the antigen, wherein the sequence encoding a type II transmembrane sequence is 5' to the insertion site, and a solid phase comprising a first oligonucleotide comprising a sequence complementary to an antigen mRNA and a second oligonucleotide comprising a sequence complementary to an immune cell receptor mRNA. In some embodiments of the kit, the vector is a DNA vector or an RNA vector. In some embodiments of the kit, the sequence complementary to the antigen mRNA or immune cell receptor mRNA comprises a sequence complementary to a portion of mRNA encoding the antigen or a portion of mRNA encoding the immune cell receptor. In some embodiments of the kit: (a) the first oligonucleotide further comprises an oligo dT sequence, (b) the second oligonucleotide further comprises an oligo dT sequence, or both (a) and (b). In some embodiments of the kit, the solid phase comprises beads. In some embodiments of the kit, the insertion site comprises the sequence encoding the antigen. In some embodiments of the kit, the vector and solid phase are configured for dropseq sequencing.

BRIEF DESCRIPTION OF THE DRAWINGS

FIG. 2A shows a schematic of an embodiment of a PDGFR construct commonly used in an MSCV vector for expressing proteins on a cell surface. Note that the transmembrane region is to the 3' end of the gene, requiring that there be no stop codons or poly-adenylation sites in the inserted sequence.

FIG. 2B shows a schematic of an embodiment of a neuraminidase construct according to the present disclosure, and designed as an alternative to the PDGFR construct. Note that the transmembrane sequence is now on the 5' end of the gene, avoiding the issues with stop codons found in the PDGFR construct.

In FIG. 8B-FIG. 8D, FPKM refers to Fragments Per Kilobase of transcript per Million mapped reads.

FIG. 9 shows an embodiment of nucleic acid sequence encoding a fusion of neuraminidase transmembrane domain and lysozyme (SEQ ID NO: 23).

FIG. 10 shows an embodiment of nucleic acid sequence encoding a fusion of lysozyme and PDGFR transmembrane domain (SEQ ID NO: 24).

FIG. 11 shows an embodiment of nucleic acid sequence of a vector (SEQ ID NO: 25) encoding a fusion of neuraminidase transmembrane domain and lysozyme.

FIG. 12 shows an embodiment of nucleic acid sequence of a vector (SEQ ID NO: 26) encoding a fusion of lysozyme and PDGFR transmembrane domain.

DETAILED DESCRIPTION

Figure 1:
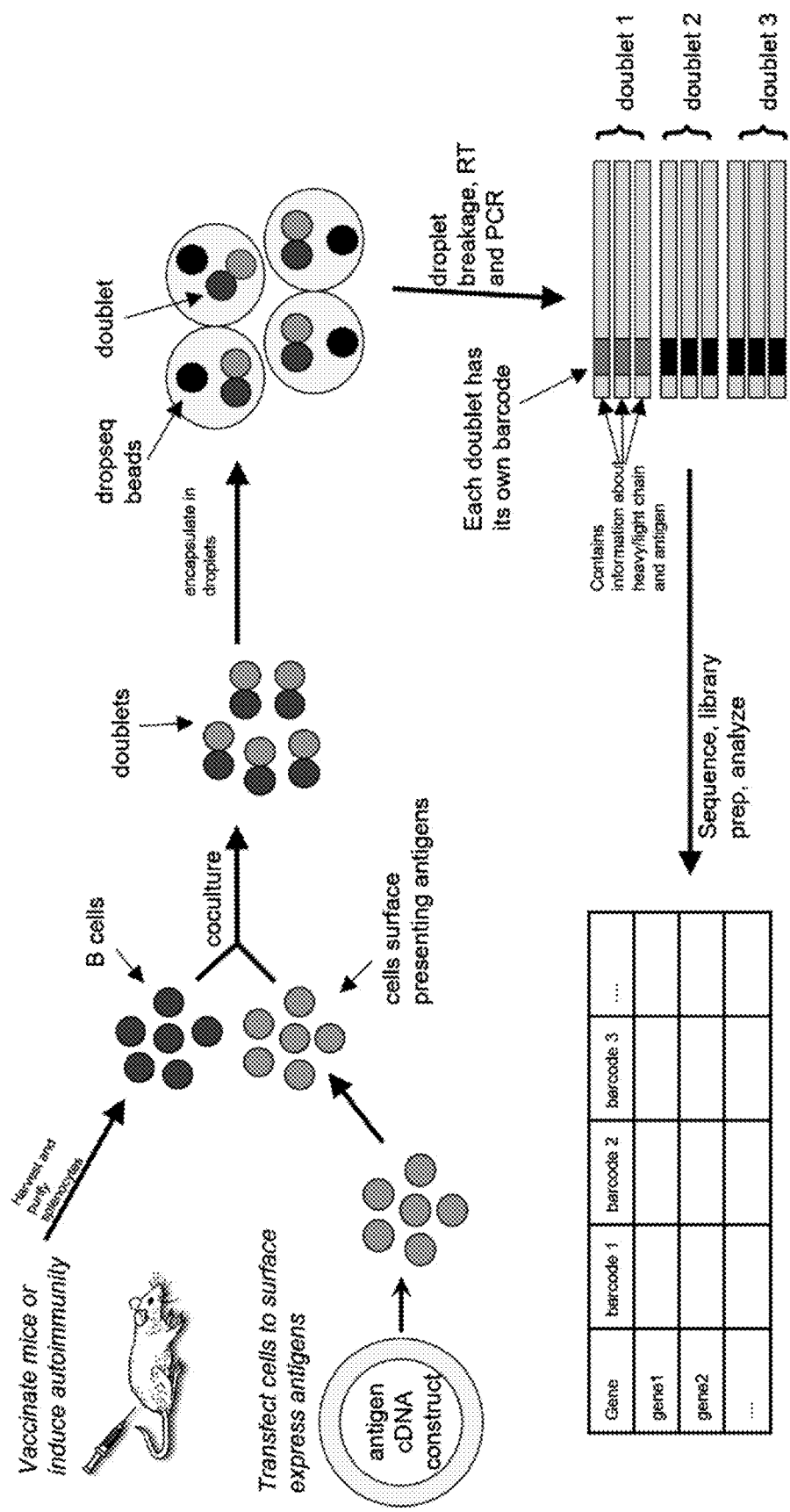
FIG. 1 shows an overview of an embodiment of a method disclosed herein.

The present disclosure is related to methods of characterizing functional immunological repertoires. In some embodiments, the methods comprise forming doublets between a cell expressing an antigen of interest on its surface and another cell expressing an antigen-specific immune cell receptor on its surface, which together form an antigen-receptor synapse. Messenger RNA (mRNA) can be isolated from a particular doublet, yielding isolated mRNA encoding the antigen (from the antigen-expressing cell) in conjunction with mRNA encoding the immune cell receptor that bound to the antigen in the doublet. The mRNA can be sequenced, for example using high-throughput sequencing to yield information about the sequences of the antigens and the immune cell receptors that bind to them. Thus, information on functional immunological repertoires can elucidated from a population of antigen-receptor pairings.

Developments in sequencing technologies have made cataloging of immune repertoire sequences a tractable endeavor. These immunological repertoires are extremely large; the B-cell repertoire is estimated to occupy nearly 1011 different combinations of sequences (Fischer, 2011), and the T-cell repertoire adds another 108 combinations to the B-cell repertoire (Nikolich-Zugich, Slifka, & Messaoudi, 2004). Antigen receptors (also referred to herein as "immune cell receptors") are formed by the products of two genes: BCRs comprise a paired heavy and light chains, and TCRs comprise a paired alpha and beta chains. Due to the extremely large size and variability of these repertoires, the advent of high throughput sequencing technologies and methods (e.g., at the single cell level of doublets of cells) have, in accordance with embodiments described herein, permitted interrogation of complete immune repertoires.

Sequencing of an immune repertoire, achieved by sequencing the two transcripts encoding the immune cell receptor proteins at the single cell level, can define the immune cell receptor repertoire.

Conventionally, two methodological approaches toward immune repertoire sequencing have been noted: (1) identifying antigen-specific receptors targeting specific pathogens or diseases, and (2) correlative investigations into the composition of the repertoire. In the first approach, the investigators physically purify lymphocytes targeting a specific disease and sequence responding cells at a single cell level. Specifically, profiling the immunological repertoire has been used to identify antibodies for pathogens such as Ebola virus and systemic lupus erythematosus (SLE; "lupus"). Alternatively, the work of some investigators identifies the correlations at the nucleic acid level between heavy and light chain proteins that compose antibodies within the immune repertoire (See, e.g., Chailyan, Marcatili, & Tramontano, 2011; DeKosky et al., 2013).

However, to the best of Applicant's knowledge, prior to this disclosure, there has been no work done to combining repertoire sequencing with determining the antigen specificity of the repertoire. A more complete description of an immunological repertoire comprises not only sequencing of immune cells receptors but also a functional elucidation of what antigens the collective memory is capable of binding. The present disclosure provides embodiments of methods, vectors, and kits, which describe an immune repertoire both genetically and functionally. In some embodiments, significant analysis and experimental data described herein have developed methods that sequence paired antigen-immune cell receptors.

Doublets

In some embodiments, the cells of a first population and cells of a second population bind to each other to form doublets of cells via formation of antigen-immune cell receptor pairs. As used herein, "doublet" refers to a pair of cells that are physically associated with each other by an antigen-receptor interaction between an antigen on one cell and an immune cell receptor on another cell. It is noted that cells that are merely in proximity to each other (but not physically associated via an immune cell receptor-antigen pairing) or cells that are physically associated with each other through a mechanism other than an immune cell receptor-antigen interaction (but are not associated with each other via any immune cell receptor-antigen interaction) are not considered to be "doublets" as used herein.

As used herein, a cell that expresses an antigen may be referred to herein as an "antigen cell" or a "bait cell," for example, in the context of a first, antigen-expressing cell of a doublet. As used herein, a cell that expresses an immune cell receptor that can bind to an antigen may be referred to herein as a "receptor cell," for example, in the context of a second, immune-cell-receptor-expressing cell of a doublet.

Thus, in some embodiments, each doublet comprises, consists essentially of, or consists of an "antigen cell" from the first population of cells expressing an antigen on the cell surface and a "receptor cell" from the second population of cells expressing an immune cell receptor on the cell surface that are physically bound to each other. In some embodiments, the doublets are stabilized. In some embodiments, a doublet is stabilized by interactions between an antigen and the immune cell receptor. Thus, a doublet represents a pairing of an antigen and its cognate immune receptor, and in some embodiments provides information about the specific antigen(s) that an immune receptor(s) binds.

In some embodiments, a method comprises isolating the doublets of cells. As used herein, an "isolated" doublet refers to a doublet that is present in an environment that is free or substantially free from other substances comprising nucleic acids that encode immune cell receptors, antigens, or both (for example, other cells, cellular debris, and/or other doublets). It will be understood that an environment comprising the doublet is substantially free of other substances (such as other doublets) when sequencing the mRNAs in that environment has at least an 85% probability of sequencing no more than one immune cell receptor clone. In some embodiments, there is at least an 86% probability that no more than one immune cell receptor will be sequenced when the mRNAs of the environment are sequenced, for example at least 86%, 87%, 88%, 89%, 90%, 91%, 92%, 93%, 94%, 95%, 96%, 97%, 98%, or 99%, including ranges between any two of the listed values. Examples of an environment in accordance with various embodiments herein include a droplet, a well in a multi-well plate, a chamber in a microfluidic device, and the like. In some embodiments, the environment is not in fluid communication with any other environments that may contain doublets. In some embodiments, the isolation is physical, for example by removing the doublet from other substances and/or removing other substances from the proximity of the doublet, and/or by establishing physical barriers between the doublet and other substances. In some embodiments, the isolated double is not in fluid communication with any other doublets. In some embodiments, the separation is functional, for example by destroying cell-free nucleic acids that may be in proximity of the doublet. In some embodiments, the separation is both physical and functional. In some embodiments, the doublets can be isolated using techniques such as cell sorting techniques, for example, Fluorescent Activated Cell Sorting (FACS), Magnetic-activated cell sorting (MACS), and Buoyancy Activated Cell Sorting (BACS). In some embodiments, doublets are isolated from other substances based on a gradient, for example, a mass or size gradient (it is contemplated that doublets of cells will generally be larger and more massive than the corresponding single cells that form the doublet) (e.g., Percoll gradient), filtration, centrifugation, microfluidic techniques, light microscopy-based techniques, and/or fluorescence microscopy-based techniques. For example, in some embodiments, the "antigen cell" a doublet can express a fluorescent protein and the "receptor cell" of the doublet can be incubated with a fluorescent dye that is taken up by the receptor cell prior to generation of doublets. The doublet can then be isolated be isolated by FACS and/or fluorescence microscopy based on the fluorescence of the fluorescent protein of the antigen cell, fluorescence of the fluorescent dye of the receptor cell, or both.

In some embodiments, the ratio of antigen cells to immune cells yielding efficient doublet formation ranges from about 1:10 to about 1:500. In some embodiments, the ratio of antigen cells to immune cells required for efficient doublet formation is about 10:1, 5:1, 1:1, 1:5, 1:10, 1:50, 1:100, 1:200, 1:300, 1:400, 1:500, 1:600, 1:700, 1:800, 1:900, or 1:1000, or a ratio within a range defined by any two of the aforementioned ratios. In some embodiments, the efficiency of doublet formation is at least 90%. In some embodiments, the efficiency of doublet formation ranges from about 90% to about 99%. In some embodiments, the efficiency of doublet formation is about 90, 91, 92, 93, 94, 95, 96, 97, 98, or 99%, or a value within a range defined by any two of the aforementioned values.

Cell Types

In some embodiments, the antigen cell (or "bait cell") is derived from a population of cells that express heterogeneous repertoire of antigens. In some embodiments, the antigens can be derived from one or more autologous proteins. In some embodiments, the antigens can be derived from one or more non-autologous proteins. In some embodiments, the antigens can be derived from one or more autologous and non-autologous proteins. Non-limiting examples of antigens include parasitic proteins, viral proteins, bacterial proteins, parasitic antigens, viral antigens, bacterial antigens, proteins that induce autoimmune disease, autoantigens, tumor proteins, tumor antigens, cancer proteins, cancer antigens, exogenous antigens, endogenous antigens, neo-antigens, toxins, and the like. It is contemplated that any number of cell types can be suitably used as antigen cells. Non-limiting examples include mammalian cell lines such as Chinese hamster ovary (CHO) cell, human embryonic kidney (HEK) cells (e.g., HEK-293T cells), human embryonic retinal cells (e.g., Crucell's Per.C6), human amniocyte cells (e.g., Glycotope and CEVEC), primate cell lines, mouse cell lines (e.g., mouse myeloma lymphoblastoid cell line, EL-4 cells, and CH12 cells), and rat cell lines. Other non-limiting examples are available from the World Wide Web at the URL en.wikipedia.org/wiki/Cell_culture#List_of_cell_lines, which is hereby incorporated by reference in its entirety. In some embodiments, for example, if the receptor cell comprises a T cell or a derivative thereof, the antigen cell further comprises a peptide on Major Histocompatibility Complexes (MHCs) to enable the formation of CD4 and/or CD8 T cell synapses for the formation of doublets as described herein.

In some embodiments, the "receptor cell" is derived from a population of cells that express heterogeneous repertoire of immune cell receptors. In some embodiments, the receptor cell comprises, consists of, or consists essentially of a lymphocyte. In some embodiments, the lymphocyte is selected from the group consisting of B cells, CD4 T cells, CD8 T cells, Gamma-Delta T cells, NK T cells, tumor-infiltrating lymphocytes, and any hematopoietically-derived cells. In some embodiments, the cells of the second population (of receptor cells) are the same type of lymphocytes (e.g., only B lymphocytes). In some embodiments, the cells of the second population (of receptor cells) are different type of lymphocytes (e.g., a mixture of B lymphocytes and T lymphocytes). Non-limiting examples of immune cell receptors include pattern recognition receptors (PRRs), Toll-like receptors, nucleotide-binding oligomerization domain (NOD)-like receptors, killer activated receptors (KARs), killer inhibitor receptors (KIRs), BCRs, TCRs, complement receptors, Fc receptors, and cytokine receptors.

Sequencing Technologies

In some embodiments, nucleic acids (e.g., mRNAs and/or cDNAs) encoding the antigen and the cognate immune cell receptor from a doublet are sequenced. In some embodiments, respective nucleic acids encoding the antigen and cognate immune cell receptor from each of a population of doublets are sequenced, thereby obtaining sequence information of a repertoire of antigens and a repertoire of immune cell receptors that bind each other.

A number of sequencing techniques are suitable for use in accordance with various embodiments herein. In some embodiments, droplet-based high throughput sequencing of these conjugate pairs reveals paired information about the receptor proteins and the antigenic proteins they respond to and/or are capable of responding to. In some embodiments, any next-generation/high-throughput sequencing technology currently known and/or in development can be used to perform the sequence analyses disclosed herein. Non-limiting examples include massively parallel signature sequencing (MPSS), polony sequencing, single-molecule real-time sequencing (Pacific Biosciences) Illumina (Solexa) sequencing, Roche 454 sequencing, ion torrent semiconductor sequencing, sequencing by ligation (SOLiD) sequencing, pyrosequencing, shotgun sequencing, nanopore sequencing, chain termination (Sanger) sequencing), DNA nanoball sequencing, heliscope single molecule sequencing, and single molecule real time (SMRT) sequencing.

In some embodiments, functional antigen-receptor synapses are formed by contacting a first population of cells expressing an antigen on the cell surface with a second population of cells expressing an immune cell receptor on the cell surface.

In some embodiments, the sequencing method is an emulsion-based bead sequencing method. In some embodiments, the emulsion-based bead sequencing method comprises droplet sequencing. In some embodiments, the emulsion-based bead sequencing method comprises droplet sequencing comprising dropseq beads (dropseq bead sequencing). In some embodiments, droplets are generated, wherein each droplet comprises a doublet of cells and a dropseq bead. The doublets within the droplets are then sequenced using droplet sequencing. In some embodiments, using bioinformatics tools (e.g., tools such as BLAST available from the World Wide Web at the URL blast.ncbi.nlm.nih.gov/Blast.cgi?CMD=Web&PAGE_TYPE=BlastHome, which is hereby incorporated by reference in its entirety, and CLUSTALW2/CLUSTAL OMEGA available from the World Wide Web at the URL clustal.org, which is hereby incorporated by reference in its entirety, for multiple sequence alignment, pairwise sequence alignment, and the like) the sequence information obtained using high-throughput sequencing is aligned with a genomic sequence of the second cells of the doublet (e.g., human or mouse genome) and the genomic sequence of the bait cells to correlate antigen and immune cell receptor sequences. As a result, a gene expression matrix is generated that displays the antigen and immune cell receptor sequences in each pair. In some embodiments, this approach enables the precise determination of antigens and/or receptors that may be useful when targeting a particular disease. In some embodiments, the high-throughput sequencing approach can be used for a myriad of diseases.

It is noted that nucleic acids that are complementary to targets can be useful in methods and kits of various embodiments herein, for example for isolating, amplifying and/or detecting target nucleic acids. As used herein, a nucleic acids that is "complementary" to its target is configured to hybridize to its target nucleic acid under amplification conditions, and can either be fully complementary to the full length of the target nucleic acid (i.e., 100% identical), or can be partially complementary to one or more portions of the target nucleic acid. In some embodiments, partially complementary refers to <100% identical, for example, about 50% to about 99.9% identical. In some embodiments, partially complementary refers about 50, 60, 70, 80, 90, 91, 92, 93, 94, 95, 96, 97, 98, 99, 99.1, 99.2, 99.3, 99.4, 99.5, 99.6, 99.7, 99.8 or 99.9% identical, or a value within a range defined by any two of the aforementioned values.

Methods of Characterizing Functional Antigen-Receptor Synapses

In some embodiments, methods for high-throughput sequencing of functional immune repertoires is described. The information obtained by these methods can provide information about the sequences of individual immune cell receptor-antigen pairings in the repertoire. In some embodiments, the methods of the present disclosure can correlate BCRs to the antigens that they recognize and bind. In some embodiments, the methods of the present disclosure can correlate TCRs to the antigens that they recognize and bind. In some embodiments, the methods of the present disclosure can correlate BCRs and TCRs to the antigens that they recognize and bind. In some embodiments, the methods of the present disclosure can correlate other immune receptors to the antigens that they recognize and bind, for example, pattern recognition receptors (PRRs), Toll-like receptors, nucleotide-binding oligomerization domain (NOD)-like receptors, killer activated receptors (KARs), killer inhibitor receptors (KIRs), BCRs, TCRs, complement receptors, Fc receptors, and cytokine receptors. In some embodiments, the methods can quantify the representation of one or more antigens in an immune response. In some embodiments, the percentage of a population of immune synapses that comprise a particular antigen can be determined. In some embodiments, if the representation of two or more antigens is being ascertained, the percentage of a population of immune synapses that comprise each antigen can be determined. In some embodiments, the number (and/or percent representation) of autoantigens in an immune response is ascertained.

Some embodiments describe methods to sequence and functionally characterize immunological repertoires. In some embodiments, functional antigen-receptor synapses or conjugates are formed between cells expressing an antigen of interest and cells expressing a receptor specific to the antigen of interest. In some embodiments, the disclosure is related to conjugates formed between one or more cell lines expressing an antigen of interest and cells expressing a receptor specific to the antigen of interest.

In some embodiments, the methods of the present disclosure phenotypically profile a functional immune repertoire. In some embodiments, the methods can provide quantitative information on an immune response. For example, if a sample from a mammal is queried for immune cell autoreactivity, a conventional approach such as an enzyme-linked immunosorbent assay (ELISA) may be able to identify that autoreactivity is present, but does not necessarily identify which antigens are responsible for the autoreactivity, much less which immune cell receptors. Without being limited by theory, it is contemplated herein that it can be useful to query to what degree that immune response represents an autoimmune response. Accordingly, methods of some embodiments can ascertain the identities of a repertoire of antigens that are involved in a particular immune response to a sample (for example, a tissue sample such as serum, peripheral blood mononuclear cells (PBMCs), whole blood, epithelial cells, or tissue of a solid organ). Moreover, in some embodiments, the methods can inform the repertoire of immune cell receptors that are involved in the autoimmune response). In some embodiments, the sample includes, without limitations, saliva, sputum, serum, plasma, lymph, cerebrospinal fluid, blood, urine, cells from a biopsy, cells from a tissue, PBMCs. In some embodiments, the mammal is human. In some embodiments, the sample is from a non-human mammal, or a non-mammalian animal. Example non-human mammals and non-mammals include, but are not limited to, mouse, rat, rabbit, sheep, goat, pig, duck, chicken, Guinea pig, dog, cow, and the like.

In some embodiments, the present disclosure describes methods of isolating individual components of functional antigen-receptor synapses (functional antigen-receptor pairs). FIG. 1 shows a schematic of an embodiment of a method according to the present disclosure. In some embodiments, functional antigen-receptor synapses are formed by contacting a first population of cells expressing an antigen on the cell surface with a second population of cells expressing an immune cell receptor on the cell surface. The pairing of the immune cell receptor with the antigen can cause a doublet to be formed. Individual doubles can be isolated, and the nucleic acids encoding the particular immune cell receptor an antigen of the functional pairing can be sequenced. Embodiments herein can be adapted for determining the immune repertoire of any immune cell, for example, B cell immune repertoire or T cell immune repertoire.

Methods of Determining the Sequence of the Antigen-Immune Cell Receptor Pair in Each Doublet In some embodiments, the methods provided herein comprise determining the sequence of the antigen-immune cell receptor pair in each doublet. In some embodiments, by determining the sequence of the antigen-immune cell receptor pair in each doublet, the individual components of each doublet are isolated. In some embodiments, the individual components represent functional receptor-antigen synapses. In some embodiments, the functional receptor-antigen synapses comprise an immunological repertoire.

In some embodiments, a first population of cells expresses a heterogeneous repertoire of antigens and a second population of cells expresses a heterogeneous repertoire of immune cell receptors. In some embodiments, by determining the sequence of the antigen-immune cell receptor pair in each doublet in a population of doublets wherein each doublet comprises a first cell (e.g., an antigen cell) from a first population of cells expressing a heterogeneous repertoire of antigens and a second cell (e.g., a receptor cell) from a second population of cells expressing a heterogeneous repertoire of immune cell receptors, functional receptor-antigen synapses that comprise a heterogeneous immunological repertoire can be determined.

In some embodiments, the functional receptor-antigen synapses that comprise a heterogeneous immunological repertoire can provide a snapshot of the antigen-immune receptor pairs of a disease at any time point. In some embodiments, by comparing the functional receptor-antigen synapses that comprise a heterogeneous immunological repertoire of a disease at different points in time, information regarding the progression of the disease and/or evolution of the profile of antigen-immune receptor pairs of the disease over time can be ascertained. In some embodiments, for chronic diseases (e.g., cancer, malaria, tuberculosis, Sjögren's syndrome, lupus, and the like) such a comparison can aid in developing vaccines and/or drugs that are tailored for administration based on the state of the disease. For example, in some embodiments, a change in the number and/or types of antigen-immune receptor pairs of a disease over time may indicate amelioration and/or worsening of the disease over time. In some embodiments, a change in the number and/or types of antigen-immune receptor pairs of a disease over time can be indicative of whether or not the disease is responding to a particular treatment strategy.

Methods of Sequencing mRNAs of a Doublet of Cells

In some embodiments, a method of sequencing mRNAs of a doublet of cells is described. In some embodiments, the doublet comprises a first cell and a second cell. The first and second cells in a doublet can form an immunological synapse. In some embodiments, the immunological synapse is formed between an antigen expressed on the first cell surface and an immune cell receptor expressed on the second cell surface. The first cell can be an "antigen cell" as described herein, and the second cell can be a "receptor cell" as described herein.

In some embodiments, methods of sequencing mRNAs of a doublet of cells comprise extracting mRNA from the antigen cell and receptor cell of the isolated doublet. In some embodiments, the doublet is isolated prior to extracting mRNA, for example using flow cytometry, FACS, MACS, BACS, a mass or size gradient, filtration, centrifugation, microfluidic techniques, light microscopy-based techniques, and/or fluorescence microscopy-based techniques. In some embodiments, mRNA can be extracted from the isolated doublet using methods that are well-known in the art. For example RNA can be extracted by cell lysis, immobilization of mRNA on a solid phase, washing, and elution of bound RNA. Additional non-limiting examples of mRNA extraction include column purification, and phenol-chloroform extraction. In some embodiments, RNA extraction comprises, consists or, or consists essentially of reverse transcription, which can be performed using non-specific (e.g., random) primers, or primers specific for a target sequence, for example, sequences encoding antigen and/or immune cell receptor polypeptides. Optionally, DNA can be digested in conjunction with reverse transcription so as to enrich for RNA-derived sequences.

In some embodiments, the mRNA from the antigen cell encodes the antigen. In some embodiments, the antigen cell is derived from a population of cells that express a heterogeneous repertoire of antigens. Thus, in some embodiments, mRNAs isolated from a population of cells encode a heterogeneous repertoire of antigens.

In some embodiments, the mRNA from the receptor cell encodes the immune cell receptor. In some embodiments, the receptor cell is derived from a population of cells that express a heterogeneous repertoire of immune cell receptor. Thus, in some embodiments, mRNAs isolated from a population of cells encode a heterogeneous repertoire of immune cell receptors.

In some embodiments, the isolated mRNAs are contacted with a solid phase. Suitable examples of solid phases that can be used in some embodiments include, but are not limited to, beads, plates, tubes, vials, nanoparticles (e.g., nanospheres, nanodiscs, nanocylinders, nanoplates, nanorods, nanopyramids, nanorings, and the like), and the like. In some embodiments, the solid phase comprises a dropseq bead.

In some embodiments, the solid phase comprises a first oligonucleotide and a second oligonucleotide. In some embodiments, the oligonucleotides are immobilized on the surface of the solid phase, for example, via a covalent bond. In some embodiments, the lengths of the first and second oligonucleotides comprised by the solid phase can each range from about a 15mer to about 500mer. In some embodiments, the length can be about 10, 11, 12, 13, 14, 15, 16, 17, 18, 19, 20, 25, 30, 35, 40, 45, 50, 75, 100, 150, 200, 250, 300, 350, 400, 450, 500mer, or a value within a range defined by any two of the aforementioned values, for example a 15-500, 20-500, 50-500, 100-500, 15-300, 20-300, 50-300, 100-300, 15-200, 20-200, 50-200, 100-200, 15-100, 20-100, 50-100, 15-50, 20-50, 15-40, 20-40, 15-30, or 20-30 mer.

In some embodiments, the first oligonucleotide comprises, consists essentially of, or consists of a first sequence that is complementary to the mRNA encoding the antigen from the antigen cell. In some embodiments, the sequence that is complementary to the mRNA encoding the antigen from the antigen cell hybridizes to the mRNA encoding the antigen from the antigen cell. In some embodiments, the second oligonucleotide comprises, consists essentially of, or consists of a second sequence that is complementary to the mRNA encoding the immune cell receptor from the second cell. In some embodiments, the sequence that is complementary to the mRNA encoding the immune cell receptor from the second cell specifically binds to the mRNA encoding the immune cell receptor from the second cell. In some embodiments, the lengths of the first and second sequences can each range from about 15mer to about 50mer. In some embodiments, the length can be about 10, 11, 12, 13, 14, 15, 20, 22, 25, 27, 30, 32, 35, 37, 40, 42, 45, 47, or 50mer, or a value within a range defined by any two of the aforementioned values.

In some embodiments, the first and/or second sequence comprises, consists of, or consists essentially of a unique "barcode" sequence, which can be used to identify the oligonucleotide and/or amplicons thereof. In some embodiments, the barcode comprises, consists essentially of, or consists of a random oligonucleotide sequence, for example a random 3mer, 4mer, 5mer, 6mer, 7mer, 8mer, 9mer, 10mer, 11mer, 12mer, 13mer, 14mer, 15mer, or the like, including ranges between any two of the listed values, for example 3-10mer, 3-15mer, 5-10mer, 5-15mer, or 10-15mer.

In some embodiments, the first sequence of the first oligonucleotide is complementary to coding sequence for the antigen. In some embodiments, the second sequence of the second oligonucleotide is complementary to coding sequence for the immune cell receptor. In some embodiments, an oligonucleotide comprises, consists essentially of, or consists of a first sequence that is complementary to coding sequence for the antigen and a second sequence that is complementary to coding sequence for the immune cell receptor.

In some embodiments, the first sequence of the first oligonucleotide is complementary to a coding sequence of the mRNA encoding the antigen. In some embodiments, the first sequence of the first oligonucleotide is complementary to a non-coding sequence of the mRNA encoding the antigen for the antigen. In some embodiments, the first sequence of the first oligonucleotide is complementary to both a coding sequence and a non-coding sequence of the mRNA encoding the antigen.

In some embodiments, the second sequence of the second oligonucleotide is complementary to a coding sequence of the mRNA encoding the immune cell receptor. In some embodiments, the second sequence of the second oligonucleotide is complementary to a non-coding sequence of the mRNA encoding the antigen for the immune cell receptor. In some embodiments, the second sequence of the first oligonucleotide is complementary to both a coding sequence and a non-coding sequence of the mRNA encoding the immune cell receptor.

In some embodiments, different oligonucleotides, some of which hybridize to antigen-encoding mRNA, and some of which hybridize to immune cell receptor-coding RNA. In some embodiments, the solid phase comprises an oligonucleotide that can hybridize to antigen-encoding mRNA, receptor-coding RNA, or both. The oligonucleotide can be immobilized on the solid phase as described herein. In some embodiments, the number of oligonucleotides on the solid phase ranges from at least 1000 to about 100000. The number of first and second oligonucleotides comprised by the solid phase can be at least about 100, 500, 1000, 2500, 5000, 7500, 10000, 12500, 25000, 37500, 50000, 75000, or 100000, or a value within a range defined by any two of the aforementioned values.

In some embodiments, the specificity of the oligonucleotide sequence that is complementary to the mRNA encoding the antigen from the antigen cell can be enhanced by increasing the length of the sequence that is complementary to coding sequences of the mRNA encoding the antigen, increasing the length of the sequence that is complementary to non-coding sequences of the mRNA encoding the antigen, or both.

Thus, in some embodiments, the first oligonucleotide comprises, consists essentially of, or consists of at least one sequence that is complementary to the mRNA encoding the antigen from the antigen cell. In some embodiments, the first oligonucleotide comprises about 2 to about 10 sequences that are complementary to the mRNA encoding the antigen from the antigen cell, for example about 2, 3, 4, 5, 6, 7, 8, 9, or 10 sequences, including ranges between any two of the listed values. In some embodiments, the size of the sequence that is complementary to the mRNA encoding the antigen from the antigen cell ranges from about a 15mer to about 100mer. In some embodiments, the length can be about 10, 11, 12, 13, 14, 15, 20, 22, 25, 27, 30, 32, 35, 37, 40, 42, 45, 47, 50, 55, 60, 65, 70, 75, 80, 85, 90, 95, or 100mer, or a value within a range defined by any two of the aforementioned values.

In some embodiments, the specificity of the sequence that is complementary to the mRNA encoding the immune cell receptor from the second cell can be enhanced by increasing the length of the sequence that is complementary to the mRNA encoding the immune cell receptor, increasing the length of the sequence that is complementary to the mRNA encoding the immune cell receptor, or both.

Thus, in some embodiments, the second oligonucleotide comprises, consists essentially of, or consists of at least one sequence that is complementary to the mRNA encoding the immune cell receptor from the receptor cell. In some embodiments, the second oligonucleotide comprises about 2 to about 10 sequences that are complementary to various portions or the entirety of the mRNA encoding the immune cell receptor from the receptor cell, for example about 2, 3, 4, 5, 6, 7, 8, 9, or 10 sequences, including ranges between any two of the listed values. In some embodiments, the length of the oligonucleotide sequence that is complementary to the mRNA encoding the immune cell receptor from the receptor cell ranges from about 15mer to about 100mer. In some embodiments, the length can be about 10, 11, 12, 13, 14, 15, 20, 22, 25, 27, 30, 32, 35, 37, 40, 42, 45, 47, or 50, 55, 60, 65, 70, 75, 80, 85, 90, 95, or 100mer, or a value within a range defined by any two of the aforementioned values.

In some embodiments, immune cell receptor comprises two chains. For example, in some embodiments, the receptor cell (e.g., a lymphocyte) comprises two mRNAs that encode a single dimeric immune cell receptor that corresponds to and binds to a cognate antigen recognized by the lymphocyte. Thus, in some embodiments, mRNA encoding a first chain, a second chain, or both chains is isolated. For convenience, it will be understood that as used herein, mRNA encoding an immune cell receptor (and similar terms) is contemplated to encompass a pair of mRNAs encoding the respective chains, as well as an mRNA encoding a single chain, or even an mRNA encoding both chains (e.g., encoding a scFv or similar molecule). In some embodiments, a second oligonucleotide comprises, consists essentially of, or consists of a second sequence that is complementary to the mRNA encoding the one chain of the immune cell receptor, and a third oligonucleotide comprises, consists essentially of, or consists of a third sequence that is complementary to the mRNA encoding the other chain of the immune cell receptor. When there are multiple immune cell receptor chains, it can be useful to use barcodes on the second and third oligonucleotides in order to ascertain which pair of receptor chains encode the same receptor (e.g., in case oligonucleotides and/or amplicons are later pooled). As such, in some embodiments, the second oligonucleotide, third oligonucleotide, or each of these comprises a barcode sequence as described herein. The barcode of the second oligonucleotide and third oligonucleotide pairing can be the same, or different from each other. In some embodiments, the second oligonucleotide are third oligonucleotide are both immobilized on the same solid phase. In some embodiments, the sequence that is complementary to the mRNA encoding the second chain of the immune cell receptor from the receptor cell specifically binds to the mRNA encoding the second chain of immune cell receptor from the receptor cell.

In some embodiments, the first oligonucleotide, second oligonucleotide, third oligonucleotide, the first and second oligonucleotides, the first and third oligonucelotides, the second and third oligonucleotides, or all three further comprise one or more oligo dT sequences. As mRNAs comprise a poly A tail, the oligo dT sequence can provide specificity for isolating mRNA to the exclusion of other forms of RNA that do not comprise a poly A tail (e.g., transfer RNA (tRNA), ribosomal rRNA (rRNA), small nuclear RNA (snRNA), non-coding RNAs, and the like).

In some embodiments, mRNAs that specifically hybridize to the solid phase are converted to complementery DNA (cDNA). In some embodiments, mRNAs that specifically hybridize to the solid phase are converted to cDNAs by reverse transcriptase-polymerase chain reaction (RT PCR).

In some embodiments, sequencing of the cDNAs can be performed by techniques that are well-known in the art. In some embodiments, sequencing of the cDNAs can be performed by any of the techniques that are described herein.

Traditionally, dropseq bead sequencing has been utilized for sequencing mRNAs from single cells. Traditionally, the use of dropseq bead sequencing was discouraged for sequencing mRNAs from two or more cells in the same sequencing reaction, as it could then be difficult to ascertain which populations of transcripts were derived from which cell.

Advantageously, in the case of a doublet as described in some embodiments herein, in which an antigen cell produces antigen mRNAs that are unique from the mRNAs of a receptor cell, and a receptor cell produces receptor mRNAs that are unique from the mRNAs of the antigen cell, the mRNAs of both cells of the doublet can be sequenced in a single reaction so as to identify cognate antigen and receptor sequences of a functional immunological synapse. As provided in Examples 3 and 4, dropseq sequencing has been confirmed to efficiently and precisely identify the sequences of a receptor and antigen of a cognate pair. Thus, in some embodiments, dropseq bead sequencing is utilized for sequencing mRNA isolated from doublets of cells.

In some embodiments, dropseq bead sequencing is utilized for sequencing mRNA isolated from doublets of cells. In some embodiments, droplets for dropseq bead sequencing are generated. As used herein, a "droplet" refers to a fluid environment comprises conditions in which oligonucleotides can hybridize, and in which the droplet is configured to contain no more than one doublet. Typically, dropseq droplets are of a pico- or nano-liter scale, for example, about 100 pl, 200 pl, 300 pl, 400 pl, 500 pl, 600 pl, 700 pl, 800 pl, 900 pl, 1 nl, 2 nl, 3 nl, 4 nl, 5 nl, 6 nl, 7 nl, 8 nl, 9 nl, or 10 nl, including ranges between any two of the listed values, for example, about 100 pl-5 nl, 100 pl-2 nl, 500 pl-5 nl, 500 pl-2 nl, and the like.

In some embodiments, a droplet for sequencing comprises a doublet of cells as describe herein and oligonucleotides complementary to antigen mRNA and immune cell receptor mRNA as described herein. The oligonucleotides can be immobilized on a solid phase (e.g., a dropseq bead) in the droplet. In some embodiments, a repertoire of droplets is generated, in which the repertoire of droplets comprises doublets of cells, wherein each doublet comprises an antigen cell from a first population of cells expressing a heterogeneous repertoire of antigens and a receptor cell from a second population of cells expressing a heterogeneous repertoire of immune cell receptors. Thus, in some embodiments, the repertoire of droplets represents receptor-antigen synapses that comprise a heterogeneous immunological repertoire.

In some embodiments, it can be useful to ascertain a repertoire of immune cell receptors that binds to a single antigen. As such, in some embodiments, the doublet comprises an antigen cell from a first population of cells, in which the antigen of any two antigen cells of the first population is the same. In some embodiments, the doublet comprises an antigen cell from a first population of cells, in which the antigen of any two antigen cells of the first population is different.

In some embodiments, a population of doublets can be homogeneous such that each doublet of the population of doublets comprises an antigen cell from a first population of antigen cells, in which the antigen expressed on all antigen cells of the first population is the same and a receptor cell from a second population of receptor cells, wherein the immune cell receptor expressed on all receptor cells of the second population is the same.

In some embodiments, the doublet comprises a receptor cell from a second population of receptor cells, in which the immune cell receptor of any two cells of the second population is the same. In some embodiments, the doublet comprises a receptor cell from a second population of receptor cells, wherein the immune cell receptor of any two receptor cells of the second population is different.

In some embodiments, a population of doublets can be heterogeneous such that each doublet of the population of doublets comprises an antigen cell from a first population of antigen cells, wherein the antigen expressed on all cells of the first population is different and a receptor cell from a second population of receptor cells, in which the immune cell receptor expressed on all receptor cells of the second population is different.

In some embodiments, a doublet is sequenced in a liquid environment that contains, or has at least a 90% probability (e.g., at least 90%, 91%, 92%, 93%, 94%, 95%, 96%, 97%, 98%, or 99%) of containing no more than one doublet. For example, in some embodiments, a solution comprising doublets as described herein is diluted, and applied to a multi-well plate (e.g., 96-well plate or a 384-well plate) so that there is at least a 90% probability that any given well contains no more than one doublet. From there, mRNAs of each doublet can be sequenced in the liquid environment so as to ascertain sequence information on antigen and receptor mRNAs for cognate immune cell receptor and antigen pair as described herein.

Vectors

In some embodiments, vectors for expressing an antigen of interest so that it is displayed on a cell surface (e.g., the surface of an antigen cell) are described. The vector can comprise a sequence encoding a membrane anchor, for example, a transmembrane domain In some embodiments, a membrane anchor refers to a polypeptide sequence or combination of sequences that mediate attachment of a polypeptide to a cell membrane. In some embodiments, membrane anchors are positioned on the C terminus of the polypeptide. In some preferred embodiments, membrane anchors are positioned on the N terminus of the polypeptide. Without being limited by any particular theory, a polypeptide comprising an N terminal signal sequence can enter the endoplasmic reticulum (ER) as part of the protein secretory pathway. In the ER, the membrane anchor or portion thereof (positioned C terminal to the signal sequence) then anchors the polypeptide resulting in the polypeptide being embedded in the ER membrane. Without being limited by any particular theory, insertion of a polypeptide's membrane anchor into the ER membrane allows the anchored polypeptide to be transported via the Golgi apparatus to the cell membrane where the polypeptide embedded into the cell membrane via the membrane anchor. Accordingly, in some embodiments, the membrane anchor is positioned C terminal to the signal sequence.

In some embodiments, the membrane anchor is substantially hydrophobic. Accordingly, in some embodiments, a majority of the amino acid residues of the membrane anchor are hydrophobic. Exemplary hydrophobic amino acid residues include Valine (V), Leucine (L), Isoleucine (I), Phenylalanine (F), and Methoionine (M). In some embodiments, at least about 50% of the amino acid residues of the membrane anchor, for example about 50%, 60%, 70%, 80%, 90%, or 95% of the amino acid residues of the membrane anchor are hydrophobic. In some embodiments, a membrane anchor facilitates the attachment of a fatty acid sequence, for example a glycosylphosphatidyl-inositol (GPI) anchor, to a polypeptide.

Membrane anchor polypeptides and nucleic acid sequences encoding the same are well-known to a person skilled in the art. Exemplary transmembrane domains of *Homo sapiens* polypeptides are provided in Table 1, and are represented by membrane anchors of SEQ ID NO: 1 to SEQ ID NO: 22, or a neuraminidase transmembrane domain that is a transmembrane domain in SEQ ID NO: 23, or a PDGFR transmembrane domain that is a transmembrane domain in SEQ ID NO: 24. In some embodiments, a membrane anchor for the embodiments of the vectors for expressing an antigen of interest disclosed herein is an Influenza Neuraminidase transmembrane sequence (FIG. 2B). In some embodiments, a membrane anchor for the embodiments of the vectors for expressing an antigen of interest disclosed herein comprises, consists essentially of, or consists of a membrane anchor selected from Table 1. In some embodiments, a membrane anchor for the embodiments of the vectors for expressing an antigen of interest disclosed herein comprises, consists essentially of, or consists of a variant of a membrane anchor selected from Table 1. In some embodiments, the variant of the membrane anchor has at least about 80%, at least about 85%, at least about 90%, at least about 95%, at least about 97%, at least about 99%, or more, sequence identity to any one of the sequences of Table 1. In some embodiments, the vectors for expressing an antigen of interest comprise nucleic acid sequences encoding any one of the membrane anchors in Table 1.

TABLE 1

Exemplary *H. sapiens* membrane anchors

| Description | Sequence | SEQ ID NO: |
|---|---|---|
| last 41 aa from the C terminus of the membrane-bound form of human IgM | EGEVSADEEGFENLWATASTFIVLF LLSLFYSTTVTLFKVK | 1 |
| 4F2 cell-surface antigen heavy chain | LLLLFWLGWLGMLAGAVVIIV | 2 |
| Aminopeptidase N | KSLGILGILLGVAAVCTIIALSVV | 3 |
| Ankyrin repeat and LEM domain-containing protein | ALAWELLGASVLLIAVRWLV | 4 |
| Membrane primary amine oxidase | ILVLLILAVITIFALVCVLLV | 5 |
| Aspartyl/asparaginyl beta-hydroxylase | FFTWFMVIALLGVWTSVAVVW | 6 |
| Beta-1,4-galactosyltransferase 1 | LLVAVCALHLGVTLVYYLAG | 7 |
| Histo-blood group ABO system transferase | GYGVLSPRSLMPGSLERGFCM | 8 |

TABLE 1-continued

Exemplary *H. sapiens* membrane anchors

| Description | Sequence | SEQ ID NO: |
|---|---|---|
| Bone marrow stromal antigen 2 | KLLLGIGILVLLIIVILGVPLIIFTIKA | 9 |
| Linker for activation of T-cells family members | ELLWPGAALLVLLGVAASLCV | 10 |
| HLA class I histocompatibility antigen, A-1 antigen, A-1 alpha chain | VGHAGLVLLGAVITGAVVAAVMW | 11 |
| Fatty aldehyde dehydrogenase | LGLLLLTFLGIVAAVLV | 12 |
| B-cell receptor-associated protein 31 | LYIAGFSLLLSFLLRRLVTLI | 13 |
| Bone morphogenetic protein receptor type-1A | WLVLLISMAVCIIAMIIFSSCFCY | 14 |
| Cadherin-1 | ILGILGGILALLILILLLLLF | 15 |
| Cell adhesion molecule 1 | AVIGGVVAVVVFAMLCLLIIL | 16 |
| T-cell surface antigen CD2 | IYLIIGICGGGSLLMVFVALLVFYIT | 17 |
| CD44 antigen | WLIILASLLALALILAVCIAV | 18 |
| T-lymphocyte activation antigen CD86 | WITAVLPTVIICVMVFCLILW | 19 |
| B-cell antigen receptor complex-associated protein alpha chain | IITAEGIILLFCAVVPGTLLLF | 20 |
| Complement receptor type 1 | ALIVGTLSGTIFFILLIIFLSWIIL | 21 |
| Macrophage colony-stimulating factor 1 receptor | VVVACMSIMALLLLLLLLLY | 22 |

In some embodiments, the vector can further comprise an insertion site configured to contain a sequence encoding an antigen in-frame with the membrane anchor. The insertion site can be positioned 3' of the transmembrane domain coding sequence. Advantageously, by placing the insertion site 3' of the transmembrane domain coding sequence, even if a nucleic acid encoding an antigen receptor contains a stop codon, the stop codon will not prevent transmembrane domain and at least a part of the antigen from being expressed. In some embodiments, for example if a variety of variant antigen-coding nucleotides is being expressed, this can avoid bias against antigen-coding nucleotides that happen to contain stop codons. In some embodiments, an antigen coding sequence is present in the insertion site. In some embodiments, the insertion site comprises a multiple cloning site (MCS). In some embodiments, the insertion site comprises recombinase target sites, for example FLP-FRT or Cre-Lox sites so that a cassette encoding an antigen of interest can be inserted therein. In some embodiments, the insertion site comprises a GATEWAY system target site. In some embodiments, the vector is a DNA vector. In some embodiments, the vector is an RNA vector. DNA and RNA vectors are well-known in the art. In some embodiments, the vector is an expression vector for expressing an antigen. In some embodiments, the expression vector comprises a nucleic acid sequence encoding the antigen. In some embodiments, the expression vector enables expression of the antigen on the surface the antigen cell of the doublet disclosed herein. Non-limiting examples of expression vectors include plasmids, cosmids, phage, phagemids, bacterial artificial chromosome, yeast artificial chromosome, human artificial chromosome, fosmids, and/or viral vectors (e.g., lentiviral vectors, adenoviral vectors, adeno-associated viral (AAV) vectors, and/or retroviral vectors).

In some embodiments, more than one type of antigen can be expressed by the antigen cell. Thus, in some embodiments, the expression vector comprises nucleic acid sequences encoding more than one type of antigen. In some embodiments, different expression vectors comprise nucleic acid sequences encoding the more than one type of antigen. In some embodiments, the same expression vector comprises nucleic acid sequences encoding the more than one type of antigen. In some embodiments, a first nucleic acid sequence encoding a first type of antigen and a second nucleic acid sequence encoding a second type of antigen are part of the same expression vector and the expression vector further comprises a 2A self-cleaving peptide-encoding sequence flanked by the first nucleic acid sequence and the second nucleic acid sequence in which the first nucleic acid sequence and the second nucleic acid sequence are driven by a single promoter. 2A peptides, including variants thereof are described in U.S. Pat. No. 9,540,657, which is hereby incorporated by reference in its entirety. In some embodiments, several antigen-encoding nucleic acid sequences can be part of the same expression vector, wherein the antigen-encoding nucleic acid sequences are linked via 2A self-cleaving peptide-encoding sequences, and all the antigen-encoding nucleic acid sequences in the vector are driven by a single promoter.

In some embodiments, a suitable expression vector can be selected based on any of a number of factors, including without limitations, cell type of the antigen cell, type of antigen to be expressed, number of antigens to be expressed, type of immune cell receptor to which the antigen would bind, and the like. In some embodiments, the expression vector can be further modified and/or optimized as required. In some embodiments, promoters and other regulatory sequences (e.g., terminators, enhancers, Kozak sequences, ribosomal binding site, and the like) are well-known in the art and can be included in the vector based any of a number of factors, including without limitations, cell type of the antigen cell, type of antigen to be expressed, number of antigens to be expressed. In some embodiments, the vector can further comprise one or more nucleic acid sequences encoding proteins that allow for selection of cells that express the antigen(s). Non-limiting examples include proteins conferring resistance to antibiotic(s) for positive selection, proteins conferring sensitivity to antibiotic(s) for negative selection, and the like that are well-known in the art).

In some embodiments, the expression vector comprises a sequence encoding a type II transmembrane sequence and an insertion site configured to contain the nucleic acid sequence encoding the antigen. The sequence encoding a type II transmembrane sequence is 5' to the insertion site. The expression vector further comprises a promoter located upstream of the sequence encoding a type II transmembrane and posttranscriptional regulatory element downstream of the insertion site. When nucleic acid sequence encoding the antigen is inserted in the insertion site, the expression vector encodes a fusion protein comprising the type II transmembrane sequence and the antigen, wherein the antigen is C-terminal to the type II transmembrane sequence. The promoter and the posttranscriptional regulatory element allow for regulating the expression of the fusion protein. The fusion protein is directed via the secretory pathway of a cell to the cell surface where the type II transmembrane sequence of the fusion protein allows for insertion of the fusion protein within the membrane and cell surface expression of the antigen. In some embodiments, the expression vector additionally comprises nucleic acid sequence(s) encoding one or more tags. Non-limiting examples of tags include AviTag, Calmodulin-tag, polyglutamate tag, E-tag, FLAG-tag, HA-tag, His-tag, Myc-tag, NE-tag, S-tag, SBP-tag, Softag 1, Softag 3, Strep-tag, TC tag, V5 tag, VSV-tag, Xpress tag, Isopeptag, SpyTag, SnoopTag, BCCP, Glutathione-S-transferase-tag, Halo-Tag, Maltose binding protein-tag, Nus-tag, Thioredoxin-tag, Fc-tag, Designed Intrinsically Disordered tags containing disorder promoting amino acids, Ty tag, and fluorescent protein based-tag. In some embodiments, fluorescent protein based-tag can be green fluorescent protein, blue fluorescent protein, cyan fluorescent protein, yellow fluorescent protein, orange fluorescent protein, red fluorescent protein, or derivatives thereof. In some embodiments, tags allow for detecting expression of antigen, and sorting and/or visualizing cells expressing antigen.

In some embodiments, the expression vector is used for cell surface expression of an antigen on the surface of the antigen cell of the doublet disclosed herein. In some embodiments, the antigen cell of the doublet disclosed herein is transfected with the vector to express the antigen on the antigen cell surface. In some embodiments, the expression vector is used to generate a first population of antigen cell, each expressing one or more antigens, which are used as "bait cells." In some embodiments, the bait cells express one or more antigens associated with a disease on their surface. The bait cells can be used to isolate antigen-specific immune cells from a sample (e.g., blood, tumor biopsy, lymph node biopsy, and the like). In some embodiments, the expression vector is as described in FIG. 2B. In some embodiments, the vector is as descried in FIG. 2B and is used for expressing antigens on the surface of bait cells.

FIG. 11 shows an embodiment of nucleic acid sequence of a vector (SEQ ID NO: 25) encoding a fusion of neuraminidase transmembrane domain and lysozyme. FIG. 12 shows an embodiment of nucleic acid sequence of a vector (SEQ ID NO: 26) encoding a fusion of lysozyme and PDGFR transmembrane domain. In some embodiments, the vector comprises, consists of, or consists essentially of the vector of SEQ ID NO: 26. It is further contemplated that in some embodiments, instead of the nucleic acid sequence encoding lysozyme, either vector can comprise an insertion site as described herein, which in some embodiments can be for the insertion of an antigen coding sequence as described herein.

Kits

In some embodiments, a kit for obtaining sequence information of an antigen and an immune cell receptor that binds to the antigen is described. In some embodiments, the kit comprises any of the embodiments of the vectors described herein.

In some embodiments, the kit further comprises a solid phase comprising a first oligonucleotide comprising a sequence complementary to an antigen mRNA and a second oligonucleotide comprising a sequence complementary to an immune cell receptor mRNA. In some embodiments, the kit further comprises a solid phase comprising a third oligonucleotide comprising a sequence complementary to an immune cell receptor mRNA. In some embodiments, the solid phase can be any of the solid phases described herein. In some embodiments, the sequence complementary to an antigen mRNA is specific for antigen mRNA, and the sequence(s) complementary to the immune cell receptor mRNA is specific for immune cell receptor mRNA.

In some embodiments, the kit comprises any of the oligonucleotides described herein. In some embodiments, the kit comprises any of the oligonucleotides described herein on any of the solid phase provided herein.

Additional Embodiments

In contrast to conventional approaches, the embodiments of the methods and kits of the present disclosure can be used to obtain a 1:1 correlation between antigens and their cognate immune receptors. Thus, the embodiments of the methods and kits herein can be used to obtain information about the antigenic repertoire that stimulates the immune system in a particular disease state (e.g., tumor antigens) and the repertoire of immune cell receptors that specifically bind to each of the antigens in the antigenic repertoire.

In some embodiments, the methods and kits of the present disclosure can reveal the "immune footprint" of a variety of diseases. For example, the methods and kits can be used to determine how a chronic disease evolves over time and/or how a chronic disease responds to treatment over time. In some embodiments, an immune footprint can be used to asses a subject's response to one or more treatments and/or vaccination evolves over time. In some embodiments, an immune footprint can inform vaccination and/or treatment strategies based on the evolution of a disease.

The methods and kits of the present disclosure can be used for quantitative assessment of a disease state. In some embodiments, the embodiments of the methods and kits provided herein can be used for highly sensitive and quantitative assessment of a disease state. For example, the current gold standard for whether or not a subject has lupus is based on an ELISA assay that provides a binary output based on the whether or not the level of an antigen is above a certain threshold. However, the ELISA assay does not provide a quantitate assessment of a disease in a subject on a spectrum of disease severity (e.g., mild<moderate<severe). The embodiments of the methods and kits provided herein can be employed to obtain a quantitate assessment of a disease on a spectrum of disease severity and the subject provide treatment based on the where the disease lies on the severity spectrum.

In some embodiments, the bait cells can be used to isolate disease-specific immune cells (e.g., cancer-specific B cells and/or T cells and/or other tumor infiltrating lymphocytes), for example, from PBMCs and/or lymph node biopsies. In some embodiments, the isolated cells can be used therapeutically in autologous and/or non-non-autologous treatments. For example, the isolated can be administered as a whole cell-based vaccine(s).

In some embodiments, the method and kits can be used to identify biomarkers and/or correlates of a disease state. For example, antigen cells (e.g., expressing antigen(s) that serve as autoantigens in multiple sclerosis (MS)) according to the present disclosure can be used to preemptively identify the presence of TCRs that are likely to cause autoimmunity in subjects who are genetically predisposed to developing MS. Conventional assays in genetically predisposed individuals do not provide as assessment of the propensity for the development of autoimmunity. The embodiments of the methods and kits herein can provide a quantitative estimate of the propensity for the development of autoimmunity.

In some embodiments, synapse sequencing according to the methods and kits herein can also provide information on the immunological basis of an autoimmune disorder such as lupus or MS. While it is known that autoimmune disorders result from a breakdown of discrimination of self-antigens from non-self-antigens by the immune system, the earliest triggers of autoimmune diseases have not been very well understood. Without being limited by any particular theory, this is because the conventional techniques can be unsuitable for profiling the entire repertoire of self-antigens associated with an autoimmune disease. Thus, synapse sequencing according to the methods and kits herein of doublets formed between cells expressing mouse surface proteins and autoimmune mouse B cells using some embodiments of the methods and kits herein can reveal information about surface proteins likely to be recognized as self-antigens. Large scale profiling of these self-antigens and their development over time (for example, determined using information generated from autoimmune B cells from younger versus older mice) can provide a generalized model on the evolution of an autoimmune response over time.

This approach, however, entails the presence of BCRs specific to each ailment. In some embodiments, the present methods and kits can be used to develop cDNA libraries that express certain peptides on Major Histocompatibility Complexes (MHCs) to enable the formation of CD4 and/or CD8 T cell synapses for sequencing and functionally characterizing not only the entire B cell repertoire but also the entire T cell repertoire.

Without being limited by any particular theory, it is believed that the embodiments of the present disclosure can have a significant impact on personalized medicine and human clinical trials. Modern genetic screens for specific biomarkers are not very comprehensive. The method and kits herein can provide information regarding an entire immune repertoire. For example, based on the populations of memory B and T cells, a comprehensive account of the antigens that an immune system has been exposed to during a lifetime, the diseases against which the immune system can mount an immune response, and diseases that cannot be effectively countered can be obtained. Thus, the embodiments of the methods and kits herein can be used forensic studies to obtain a comprehensive account of the antigens and/or environments that an individual's immune system has been exposed to over time and/or during a lifetime.

In summary, the embodiments provided herein described enable functional characterization of an entire immune repertoire, which has not been yet been accomplished by other approaches, and has far-reaching implications in research and personalized medicine.

EXAMPLES

The following Examples describe the components of the methods and kits and experimental verification of the different aspects of the methods and kits provided herein. The Examples are non-limiting and other variants are contemplated.

Example 1—Bait Cell Libraries

As a preliminary matter, cell lines presenting libraries of antigens of interest (bait cells) were developed. It was contemplated that such cell lines could be used in the functional characterization of immune repertoires in accordance with some embodiments herein. It was contemplated that cell lines able to surface-present any given antigen can be used in accordance with the embodiments of the methods and kits herein.

Traditional methods to achieve surface presentation of a protein of interest typically use the PDGFR transmembrane domain to insert the protein into the surface of the membrane. The layout of this vector is shown in FIG. 2A.

FIG. 2A depicts the PDGFR construct commonly used in an MSCV vector when surface presenting proteins. In this traditional construct, the PDGFR gene must be placed on the 3' end for this construct to work. It is noted that if the transmembrane (PDGFR) region is to the 3' end of the gene, there can be no stop codons or poly-adenylation sites in the inserted sequence. Therefore, presenting a large library of proteins with this traditional construct is problematic, because the encoding genes may contain endogenous stop codons. This would cause premature termination of translation, effectively preventing surface presentation.

A new surface presentation method in accordance with some embodiments herein was developed. FIG. 2B depicts a vector for expression of antigens in accordance with some embodiments herein. Such a construct (a neuraminidase construct in this particular example), represents an alternative to the traditional PDGFR construct. It is noted that the transmembrane sequence is now on the 5' end of the gene, advantageously avoiding the issues with stop codons found in the PDGFR construct. As such, in some embodiments, antigen-coding sequences can express surface-presented antigen, even if the antigen coding sequences further comprise a stop codon.

The new transmembrane construct placed neuraminidase on the 5' end of the sequence of interest. Because transcription runs from 5' to 3' on the antisense strand, endogenous stop codons no longer interfere with translation. Studies of the transmembrane properties of neuraminidase are described in Dou, da Silva, Nordholm, Wang, & Daniels, 2014).

Figure 3A:
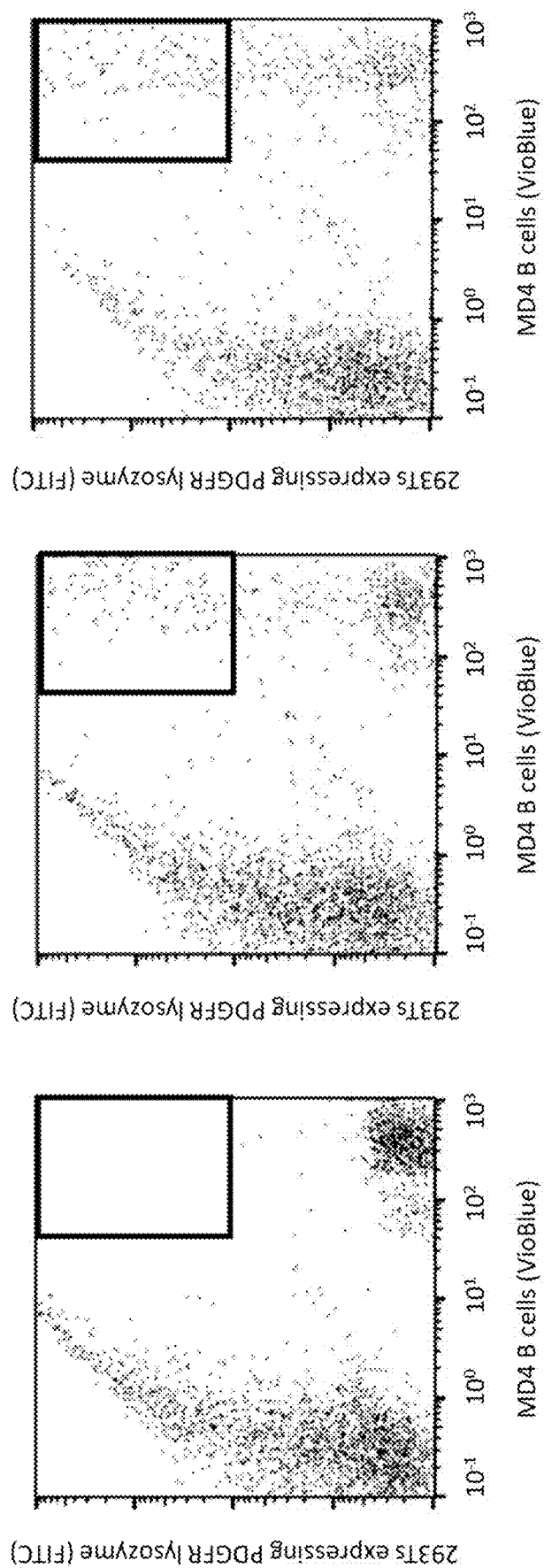
FIG. 3A shows an embodiment of FACS data related to formation of conjugates with MD4 B cells.

The construct was verified using the HEL/anti-HEL model system. Lysozyme was inserted into the cDNA of interest region. UVSE stained MD4 B cells, which present anti-HEL antibodies on their surface, were then bound to these transfected cells. As would be expected with successful lysozyme surface presentation, the MD4 cells bound more to the neuraminidase transfected cells than to cells transfected with an empty vector. The resulting FACS experiment is shown in FIG. 3A. Because the MD4 B cells are labeled with a blue stain (UVSE) and the construct contains GFP (which is green), it was possible to visualize the doublets by flowcytometry (FIG. 3A). A comparison of the flowcytometry results of the neuraminidase construct with flowcytometry results of the PDGFR construct showed that the functionality of the novel neuraminidase-based construct of the novel surface presentation system disclosed herein was similar to that of the commonly used PDGFR construct.

Figure 3B:
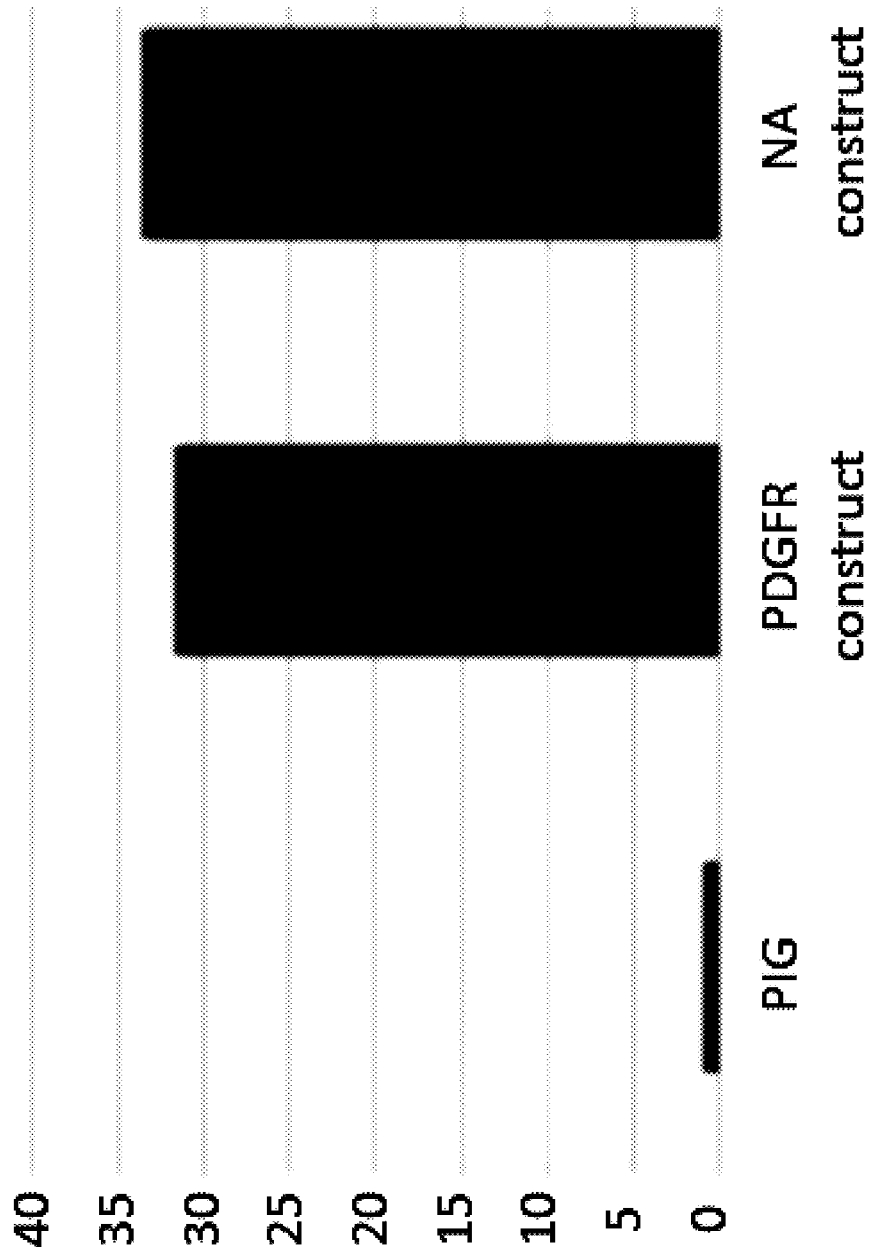
FIG. 3B shows a graph of data comparing efficacies of two constructs.
Figure 4B:
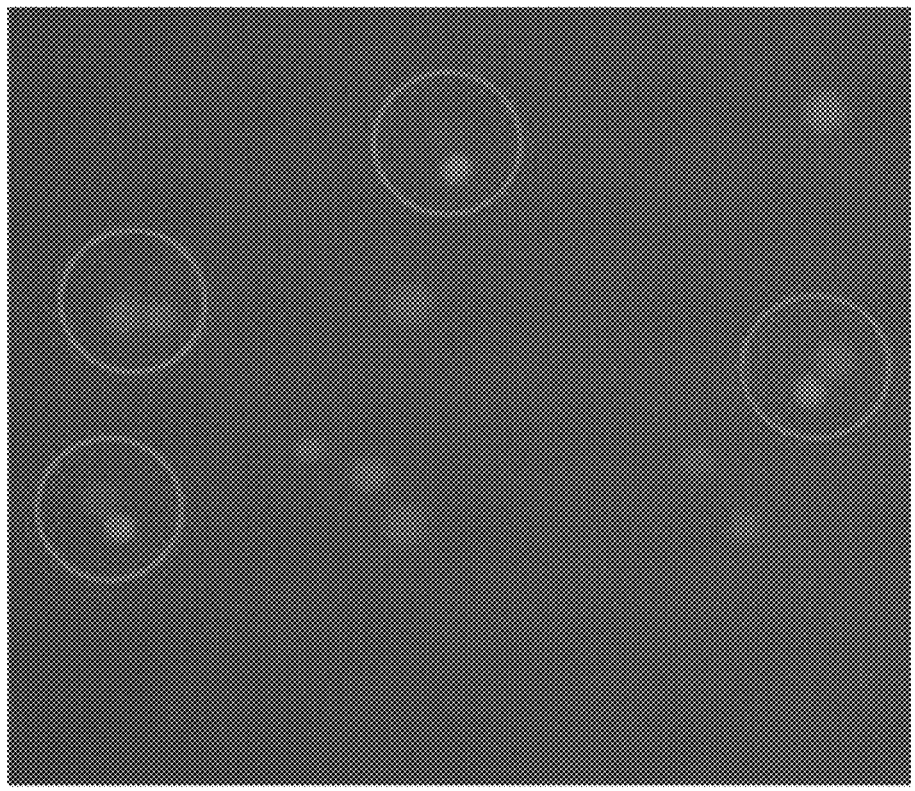
FIG. 4B shows an embodiment of an image of immunological synapses between doublets of cells by fluorescence microscopy.
Figure 4A:
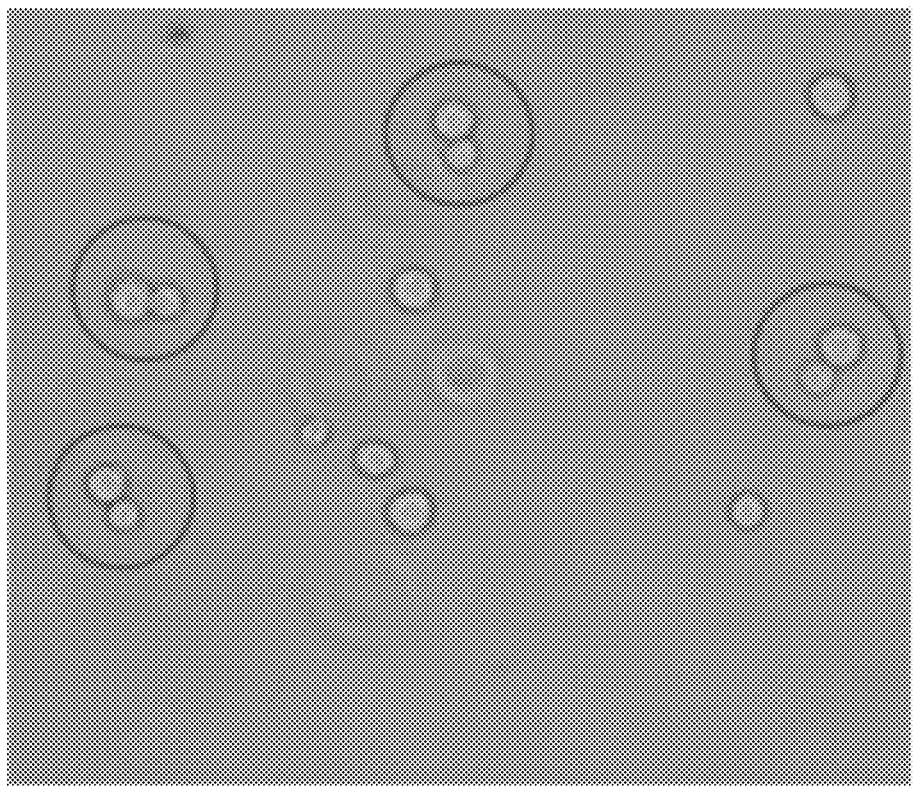
FIG. 4A shows an embodiment of an image of immunological synapses between doublets of cells by light microscopy.
Figure 5:
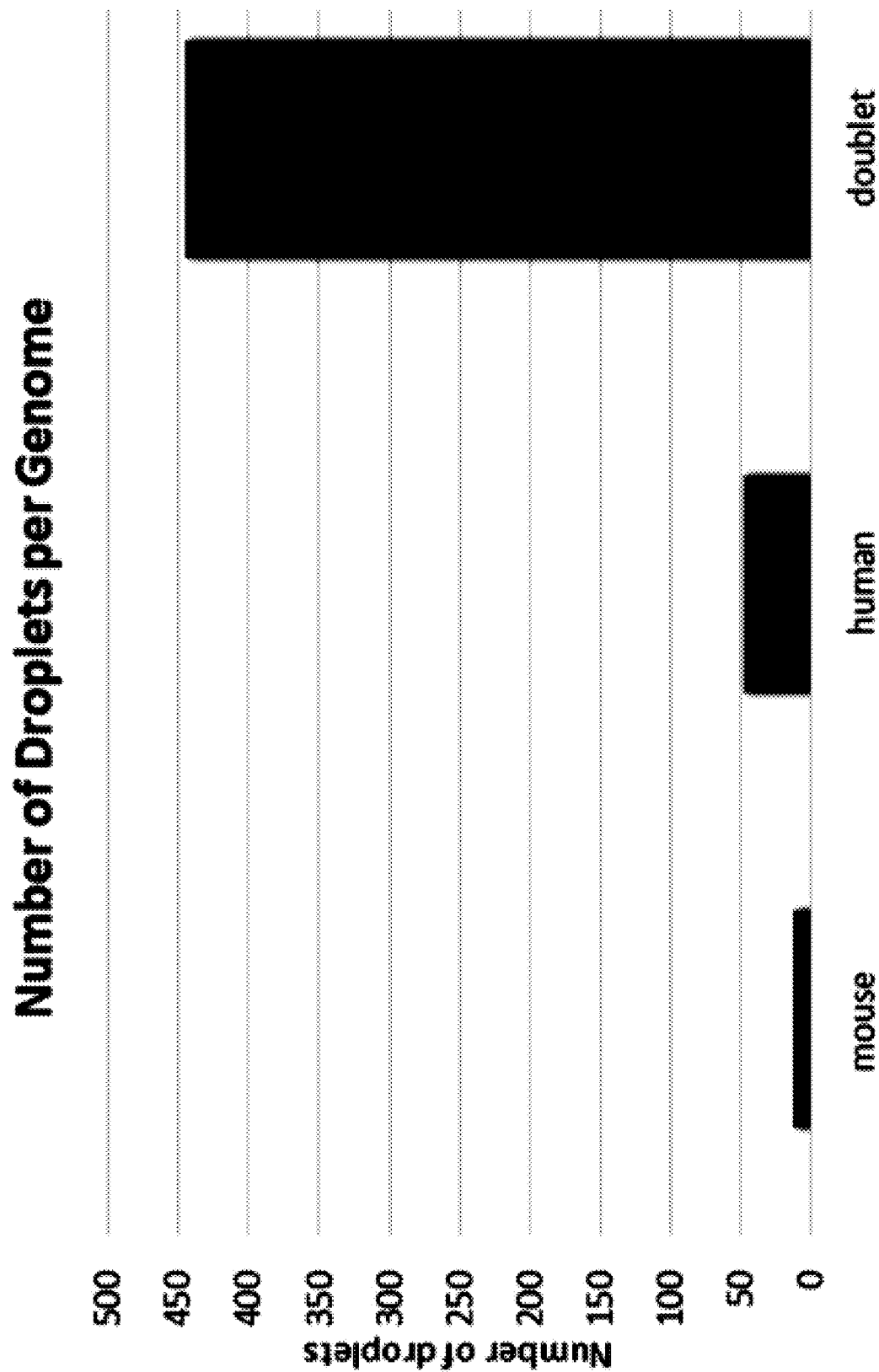
FIG. 5 shows a graph of the number of droplets that align to the genomes of the cells enclosed in the droplets.

FIG. 3A presents FACS data that displays conjugates formed with MD4 B cells and, from left to right, native 293T cells transfected with empty MSCV vector, 293T cells expressing lysozyme using PDGFR, and 293T cells expressing lysozyme using our neuraminidase construct. Both constructs generate conjugates. FIG. 3B shows that both constructs formed doublets with similar efficiency.

As the functional Neuraminidase construct has been confirmed, large libraries of antigenic sequences were generated for placement into this construct. Using mRNA purified by poly-A selection from cells containing the antigens of interest, we performed template switching reverse transcription reactions, resulting in a library of double stranded cDNA encoding antigenic proteins of interest. To facilitate insertion into the transmembrane construct, restriction sites were added onto the cDNA library using a PCR reaction with primers containing the Not1 and Sbf1 restriction sites. This library and the transmembrane vector are digested with the Not1 and Sbf1 enzymes and ligated together. The resulting construct is then transfected into 293T cells. Because the vector is an MSCV vector, the 293T cells begin to produce retroviruses containing the cDNA of interest. The virus is harvested and used to infect a cell line, effectively generating an entire cell line of bait cells presenting the library of desired antigens.

In summary, a vector construct for presentation of antigens on the surface of bait cells in accordance with some embodiments herein was successfully generated and tested in 293T cells. Additionally, a library of double stranded cDNA encoding antigenic proteins of interest was successfully generated in accordance with some embodiments herein, using this vector construct disclosed herein.

Example 2—Doublet Formation

Next, antigens were physically associated with the (cell surface-bound) antibodies they bind to. Memory B cells presenting BCRs specific to these antigens were generated by immunizing mice against the disease of interest. These B cells were then harvested from the mouse's spleen and purified. The purified B cells are co-cultured with the aforementioned cell line. This leads to the formation of what we refer to as "doublets," or a stably bound pair of cells consisting of one B cell and one bait cell. We demonstrated that some crude doublets form using a model system of MD4 B cells, which, once again, present only anti-HEL antibodies, and "bait" cells presenting Hen Eggwhite Lysozyme (HEL). FIG. 4A and FIG. 4B display light (left) and fluorescent (right) microscopy images of doublets. In particular, FIG. 4A and FIG. 4B show immunological synapses observed as cell doublets by microscopy. FIG. 4A shows Light and FIG. 4B shows fluorescent microscopy revealed cell doublets (circled) in preparations of immunological synapses between lysozyme-presenting (labeled with blue dye) and anti-lysozyme antibody-bearing cells (labeled with green dye).

The efficiency of these early co-cultures was relatively low. Thus, the procedure for forming these doublets was optimized extensively, testing the effects of duration of co-culture, temperature during co-culture, density of cells in co-culture, and ratio of B cells to target cells in co-culture. FIG. 4A and FIG. 4B display one such experiment, in which we show that nearly 90% of our B cells form doublets if we provide them with a large excess of bait cells to bind to.

In summary, doublets of cells were successfully generated and verified using light and fluorescent microscopy in accordance with some embodiments herein. Additionally, conditions required for efficient formation of doublets were established in accordance with some embodiments herein.

Example 3—Droplet Sequencing

High throughput sequencing of these doublets was performed using a droplet sequencing protocol. Droplet sequencing, and in particular barcoded bead sequencing from these cells has been developed and described, but traditionally was used for single cells (See, (Regev et al., 2016) (Weitz et al., 2009)).

There are several differences between the single-cell droplet protocols and the approaches detailed in accordance with some embodiments herein. Instead of single cells, doublets of lymphocytes and bait cells inside droplets were captured. After capture, the two cells lyse and release the mRNA within. In the original dropseq protocol shown in FIG. 1, these transcripts would then bind to the dT bead within the droplet. Each bead contains a unique oligonucleotide barcode preceding each dT sequence, enabling us to retain single cell resolution. For the method detailed within this document, these barcoded dT beads were extended to pull down antigen and antigen receptor (IgM) sequences specifically. Reverse transcription and PCR following pull-down was performed to generate a library to perform further downstream analysis and sequence. Paired-end sequencing data were then aligned to a custom genome that was generated and contained mouse genome (because the lymphocytes used were extracted from mice) along with the genome of the antigen cell line (of human origin). This yielded a matrix of gene expression that correlated each doublet (identified by a unique barcode) to the genes it contained. FIG. 5 verifies graphically that genes from both cells in the doublet were pulled down.

In summary, FIG. 5 shows data related to droplets sorted based on the genomes their enclosed cells aligned to. The majority of droplets aligned to both mouse and human genomes, indicating that the majority of droplets generate and sequences in accordance with some embodiments herein contained synapses of doublets.

Example 4—mRNA Capture

Native dropseq sequencing traditionally pulls down the entire transcriptome of the doublets. While one can still bioinformatically extract antigen receptor sequence data from the entire transcriptome, without being limited by any particular theory, it is contemplated that in accordance with some embodiments, pulling down only the transcripts specific to antigen receptors and the antigens being studied would improve the efficiency of the process and remove extraneous data from sequencing.

Thus, a method to specifically pull down mRNA transcripts was developed in accordance with some embodiments, in which the poly-T oligonucleotides on the surface of the beads were extended to contain sequences complementary to the antigen receptor and antigen sequences being studied.

IgM, the heterodimer of heavy and light chain antigen receptor proteins in the B lymphocyte, was used as a system to demonstrate antigen receptor mRNA capture. IgM-specific, sense RNA template strands were synthesized and bound to the dT beads using poly-A oligonucleotide regions (FIG. 6B). Reverse transcriptase was then used to extend the dT oligo to contain the IgM complementary sequence (FIG. 6B). Subsequent RNAse treatment degraded and removed the RNA template strand, allowing the bead to contain IgM probes that pull down RNA with specificity (FIG. 6B).

Figure 6A:
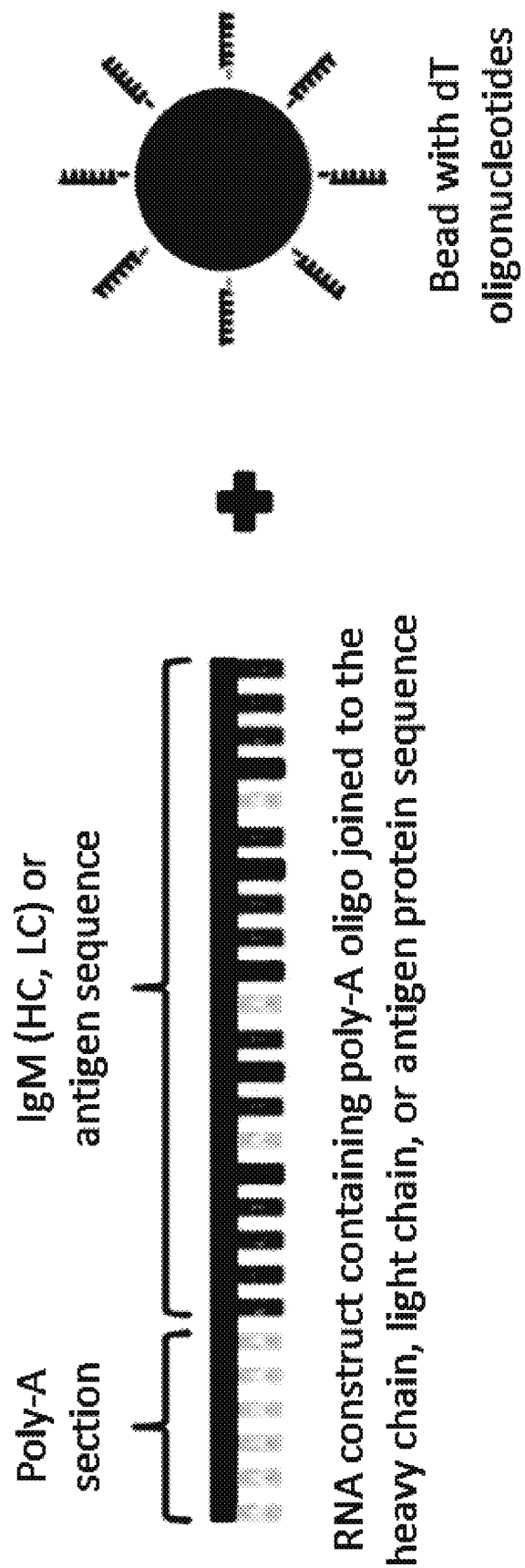
FIG. 6A-FIG. 6B show a schematic of an embodiment of a method for capturing an RNA of interest.
Figure 6B:
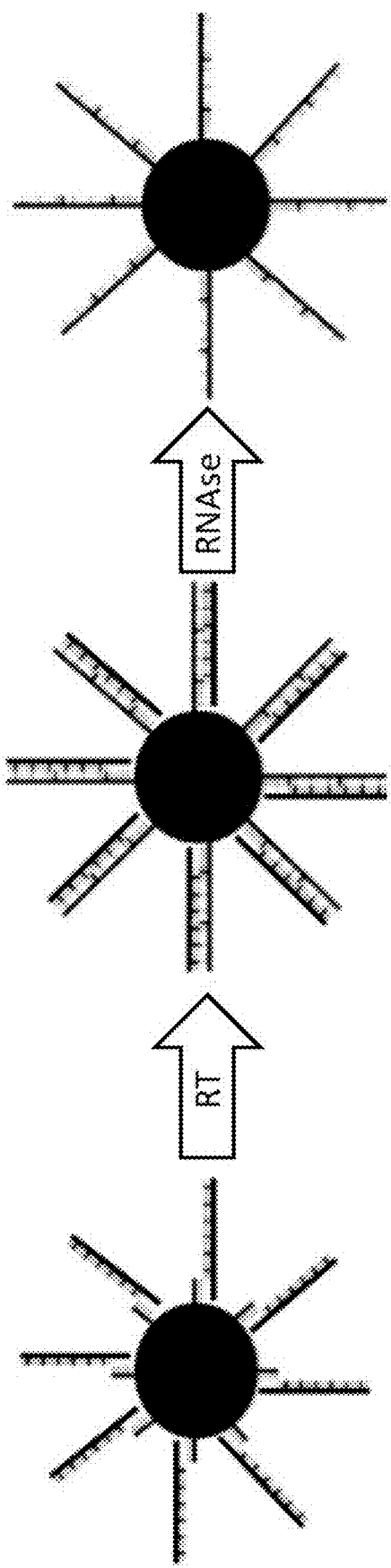

FIG. 6A shows RNA constructs containing a poly-A region and the sequence of interest were synthesized and annealed to the dT beads. As shown in FIG. 6B, these beads were then put through an RT and RNAse treatment to extend the dT oligonucleotides for specific pulldown Initial verification of these beads using binding to heavy chain oligonucleotides bound to fluorescent markers showed that the extensions were forming properly and that IgM specific hybridization was successfully obtained. This process and result are shown in FIG. 7A and FIG. 7B.

Figure 7A:
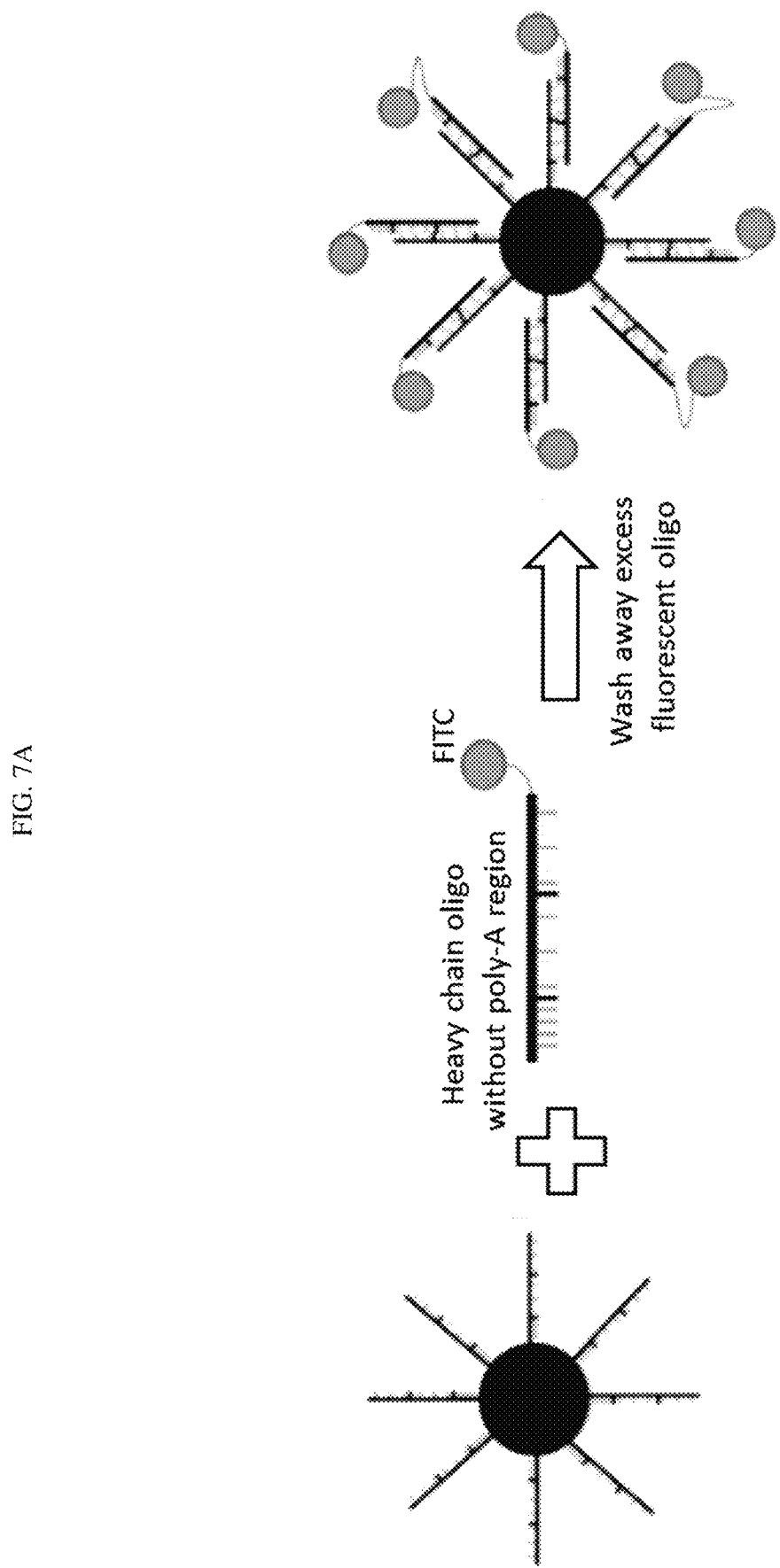
FIG. 7A-FIG. 7B show an embodiment of a method for verifying bead extension using fluorescent oligonucleotides.
Figure 7B:
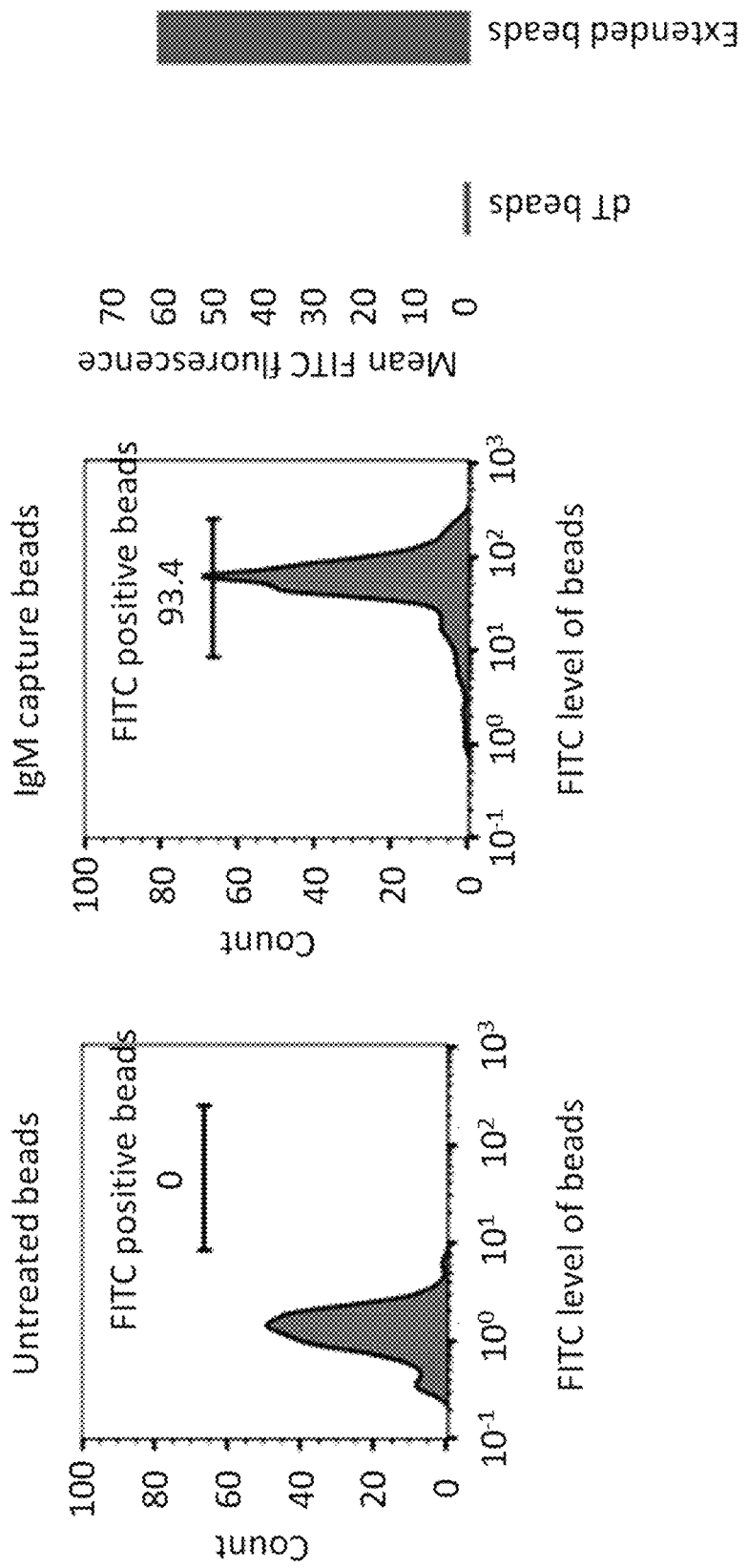

FIG. 7A shows the process used to verify bead extension using fluorescent heavy chain oligonucleotides. In FIG. 7B, FACS data show a clear increase in fluorescent signal with the extended beads, indicating that they were hybridized to the fluorescent oligonucleotides whereas the dT beads were not.

Figure 8A:
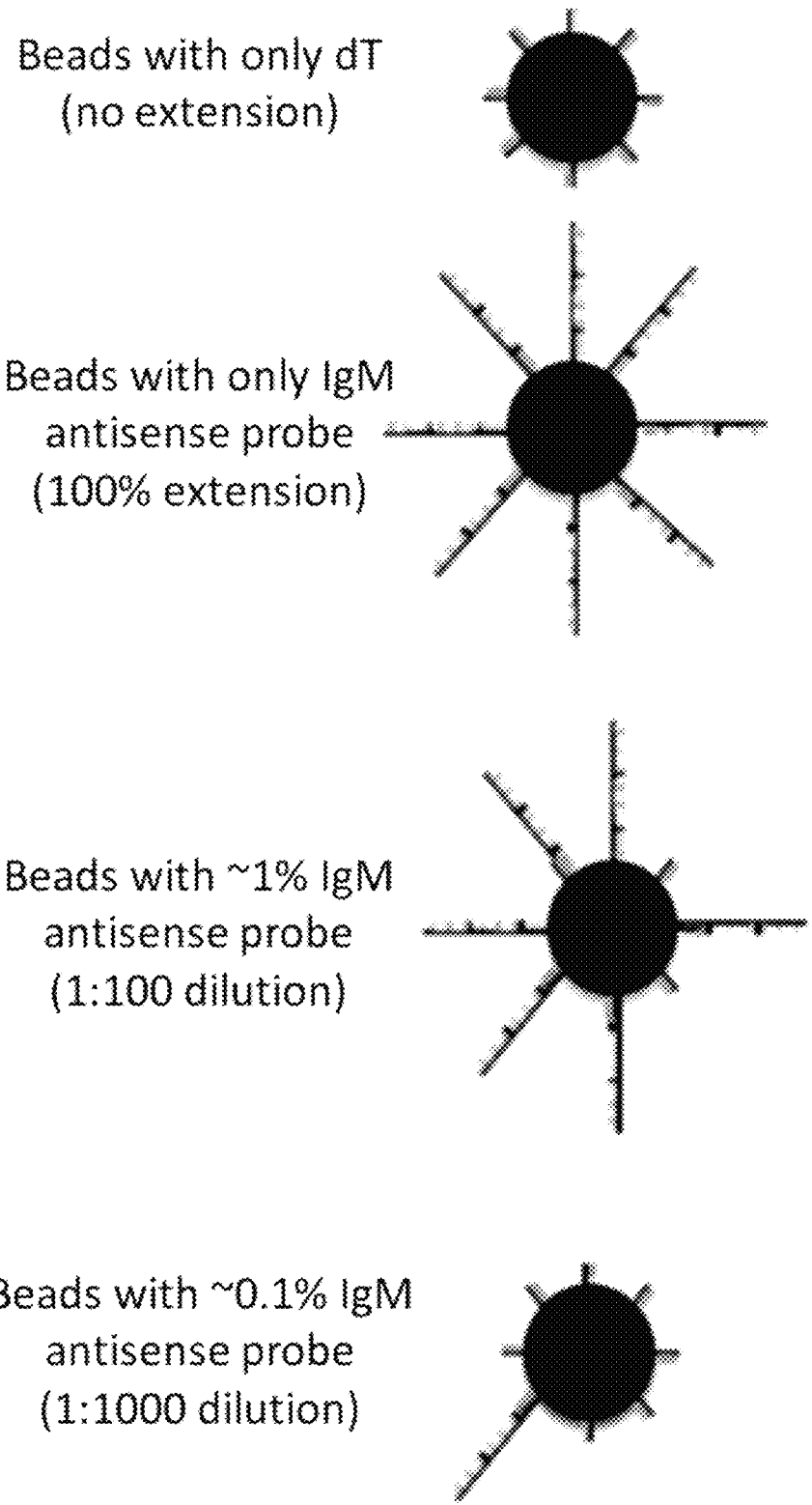
FIG. 8A-FIG. 8D show an embodiment of a method according to the present disclosure.

Running these extended beads through dropseq with doublets formed between MD4 B cells and A20 cells presenting lysozyme showed that IgM specific pulldown did indeed occur in the high throughput context (FIG. 8A). Without being limited by any particular theory, it is contemplated that in some embodiments, some of the dT oligonucleotides on the surface of the bead were left unextended in order to prevent concatemerization of the extensions during dropseq library amplification. See, FIG. 8B-FIG. 8D.

Figure 8B:
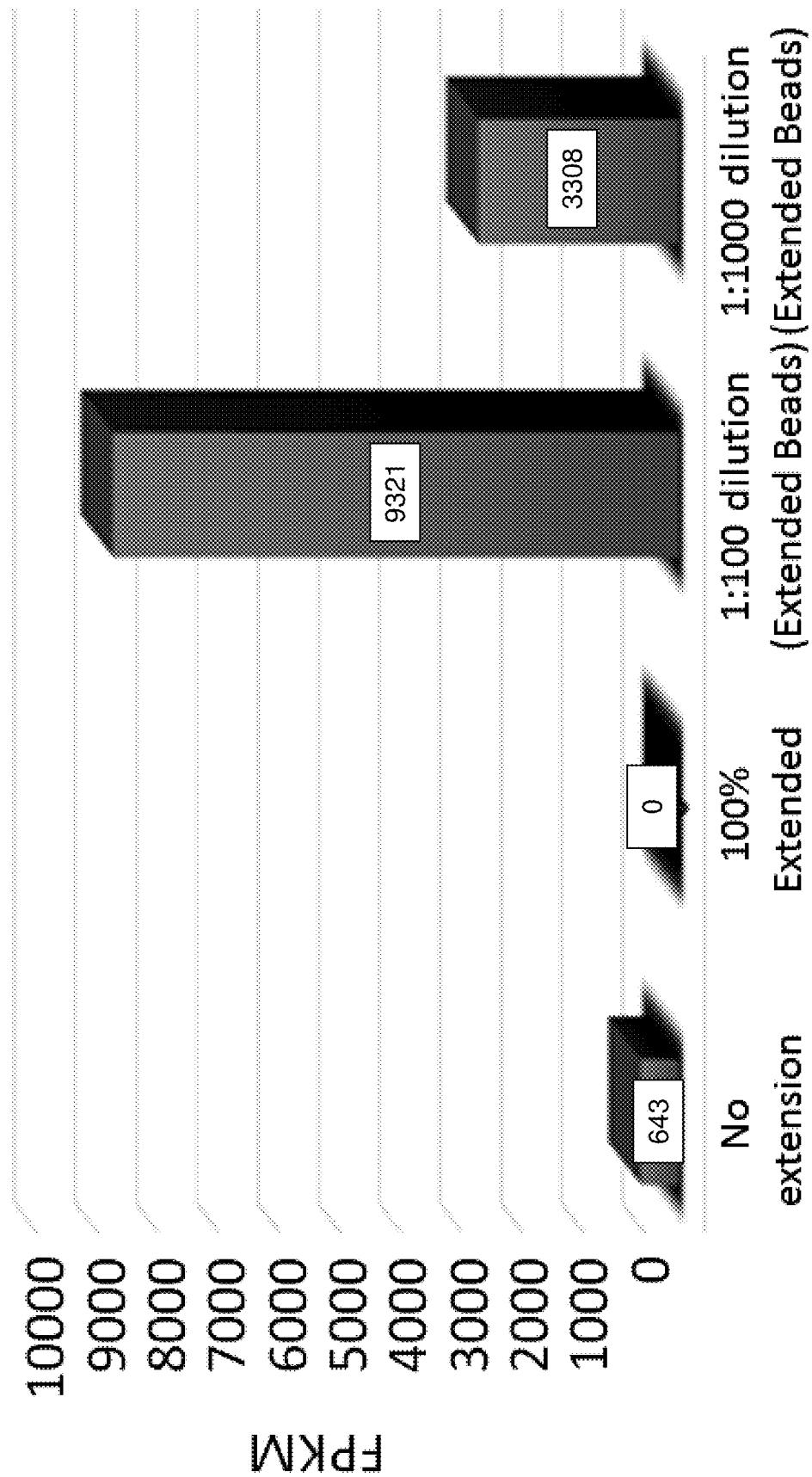
Figure 8C:
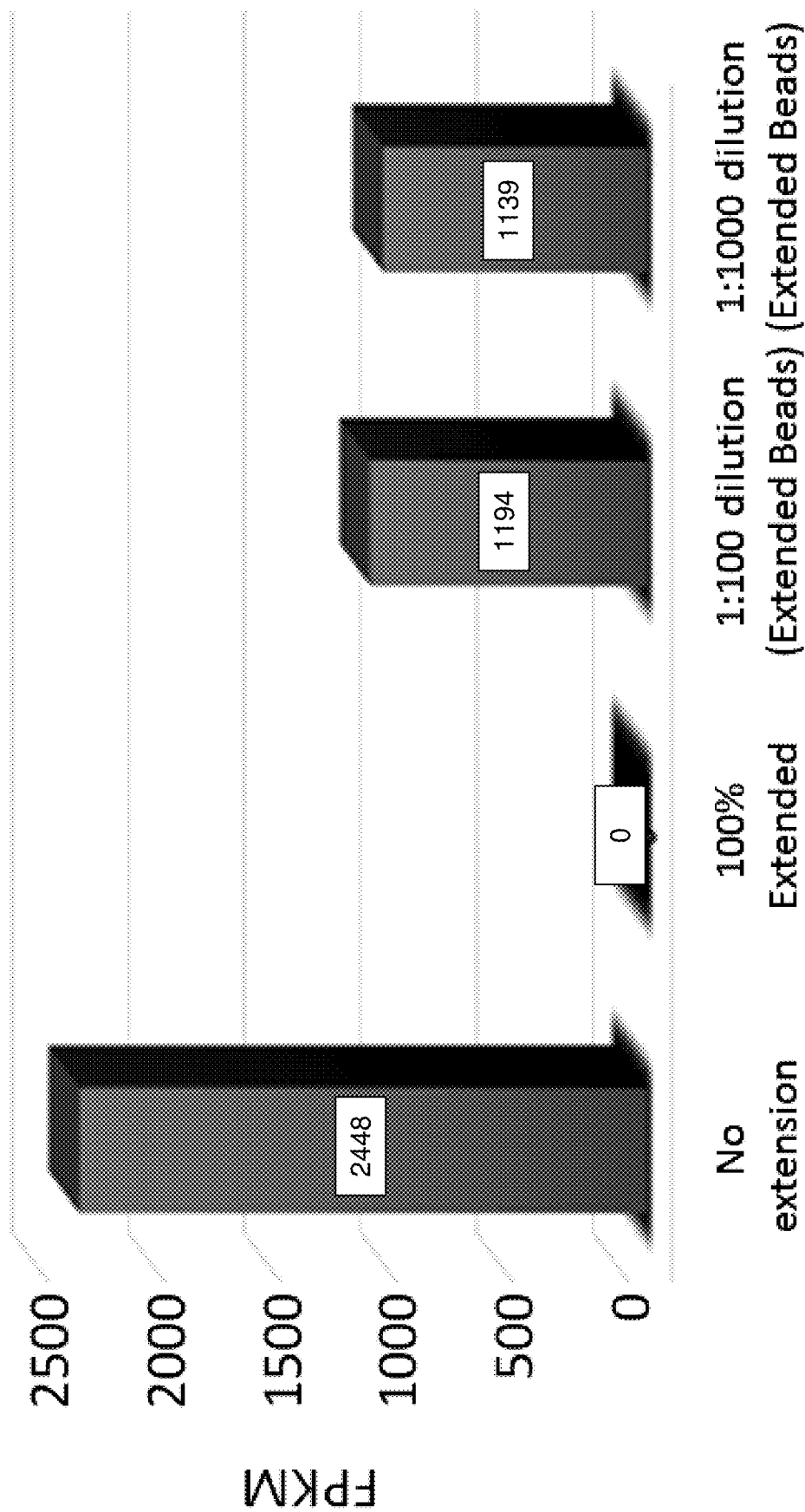
Figure 8D:
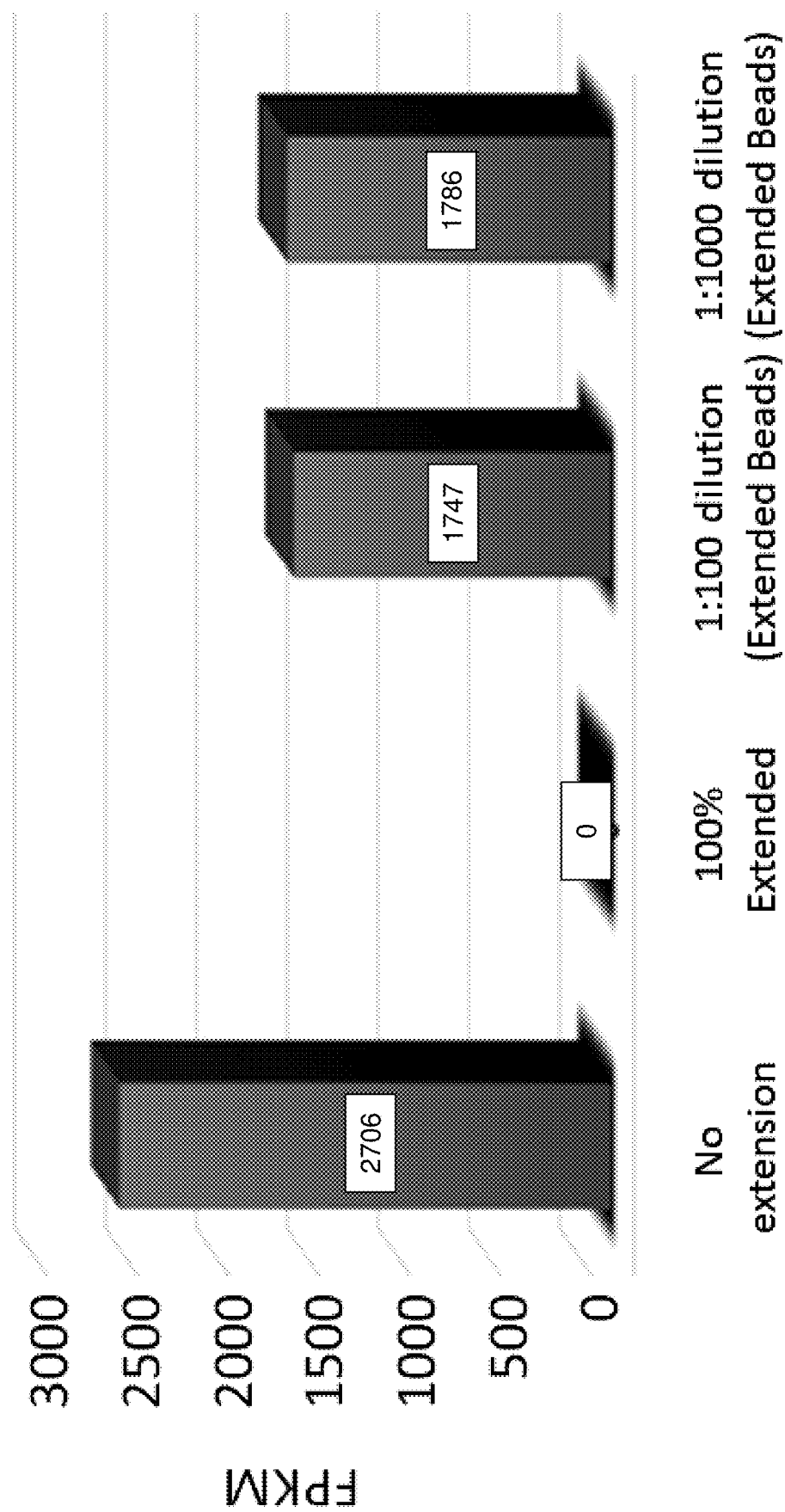

FIG. 8A depicts the beads used in this dropseq run. It is noted that different fractions of the dT oligonucleotides were extended on the surface of these beads because, as seen from sequencing data in FIG. 8B-FIG. 8D, pulldown appeared to be inhibited by concatemerization of the extensions when 100% of the dT oligonucleotides are extended. In FIG. 8B, without being limited by particular theory, IgM pulldown appeared to be enriched in the partially extended beads. FIG. 8C and FIG. 8D show that actin and L32 pulldown were reduced when pulling down with extended beads, further confirming the mechanisms of the method as described herein that pulldown appeared to be inhibited by concatemerization of the extensions when 100% of the dT oligonucleotides are extended.

In summary, dropseq beads comprising oligo dT and antigen mRNA specific sequences were generated and successfully used to isolate FITC-labeled IgM specific mRNA from B cells in accordance with some embodiments herein.

Example 5

Acute myeloid leukemia (AML) patient PBMCs are isolated from A2+ positive patients using Ficoll preparation of PBMCs. CD8 T cells are expanded for 3 days. CD8 T cells are stained with CD8-allophycocyanin (APC) antibody the day of the experiment. A library of cancer neoantigens is prepared by generating peptides from CBIOAtlas defined neoantigens and patient-specific exome sequencing. A2 binding is predicted computationally. The library of cancer neoantigens is printed on a microarray and cloned into A2 single chain trimer. A library is generated with peptide/trimer library and transfected into 293T cells. 15×10e6 293T cells are transfected with 30 µl Mirus293T in complex with 30 µg library plasmid. In order to create synapses, patient PBMCs are cultured in RPMI/10% FBS. 293T cells are solubilized with EDTA (not trypsin) and resuspended in C10. Cells were co-incubated for 15 min at 37° C. Sorting of doublets is performed by identifying doublets with APC-CD8 T cell GFP-SingleChainTrimer. Doublets are sorted into PBS and concentrated. Dropseq sequencing is performed on doublets as specified in Macosko et al.

In summary, bait cells expressing a heterogeneous repertoire of AML antigens are used to isolate doublets of AML antigen-specific CD8 T cells and dropseq sequencing is performed to identify antigen-receptor pairs in accordance with some embodiments herein.

REFERENCES

All references herein are hereby incorporated by reference in their entireties.

Chailyan, A., Marcatili, P., & Tramontano, A. (2011). The association of heavy and light chain variable domains in antibodies: implications for antigen specificity. *FEBS J*, 278(16), 2858-2866. doi:10.1111/j.1742-4658.2011.08207.x DeKosky, B. J., Ippolito, G. C., Deschner, R. P., Lavinder, J. J., Wine, Y., Rawlings, B. M., . . . Georgiou, G. (2013). High-throughput sequencing of the paired human immunoglobulin heavy and light chain repertoire. *Nat Biotechnol*, 31(2), 166-169. doi:10.1038/nbt.2492

Dou, D., da Silva, D. V., Nordholm, J., Wang, H., & Daniels, R. (2014). Type II transmembrane domain hydrophobicity dictates the cotranslational dependence for inversion. *Mol Biol Cell*, 25(21), 3363-3374. doi:10.1091/mbc.E14-04-0874

Fischer, N. (2011). Sequencing antibody repertoires: the next generation. *MAbs*, 3(1), 17-20. Accessible on the world wide web at www.ncbi.nlm.nih.gov/pubmed/21099370.

Nikolich-Zugich, J., Slifka, M. K., & Messaoudi, I. (2004). The many important facets of T-cell repertoire diversity. *Nat Rev Immunol*, 4(2), 123-132. doi:10.1038/nri1292

Regev, A., MACOSKO, E. Z., MCCARROLL, S. A., SHALEK, A. K., BASU, A., FORD, C. B., . . . Weitz, D. A. (2016). A droplet-based method and apparatus for composite single-cell nucleic acid analysis—WO2016040476 A1.

Weitz, D. A., Griffiths, A., Koester, S., Mootha, V. K., Duan, H., Agresti, J., . . . Gilbert, J. R. (2009). Droplet-based selection—US20090068170 A1.

Macosko et al.

In some embodiments, the method, kit, or vector comprises various steps or features that are present as single steps or features (as opposed to multiple steps or features). For example, in some embodiments, the method includes sequencing a single doublet. Multiple features or components are provided in some embodiments. In some embodiments, the method comprises sequencing more than one double, for example sequencing an immune repertoire that comprises multiple antigen-immune cell receptor pairings.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims. For each method described herein, relevant kits for use in the method are expressly contemplated. For example, for methods of isolating individual components of functional receptor-antigen synapses, kits comprising reagents for isolating individual components of functional receptor-antigen synapses are also contemplated. For example, for methods of sequencing a doublet, kits comprising reagents for sequencing a doublet are also contemplated.

One skilled in the art will appreciate that, for this and other processes and methods disclosed herein, the functions performed in the processes and methods can be implemented in differing order. Furthermore, the outlined steps and operations are only provided as examples, and some of the steps and operations can be optional, combined into fewer steps and operations, or expanded into additional steps and operations without detracting from the essence of the disclosed embodiments.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. For example, "about 5", shall include the number 5. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth. Numbers preceded by a term such as "approximately", "about", and "substantially" as used herein include the recited numbers (e.g., about 10%=10%), and also represent an amount close to the stated amount that still performs a desired function or achieves a desired result. For example, the terms "approximately", "about", and "substantially" may refer to an amount that is within less than 10% of, within less than 5% of, within less than 1% of, within less than 0.1% of, and within less than 0.01% of the stated amount.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

What is claimed is:

1. A method of isolating individual components of functional receptor-antigen synapses comprised by an immunological repertoire, the method comprising:
contacting:
a first population of cells expressing an antigen on the cell surface;
with
a second population of cells expressing an immune cell receptor on the cell surface,
whereby, the cells of the first population and cells of the second population bind to each other to form doublets of cells via formation of antigen-immune cell receptor pairs;
isolating the doublets of cells, wherein each doublet comprises one cell from the first population and one cell from the second population;
determining the sequence of the antigen-immune cell receptor pairs, thereby isolating individual components of functional receptor-antigen synapses comprised by an immunological repertoire.

2. The method of claim 1, wherein the first population of cells expresses a heterogeneous repertoire of antigens.

3. The method of claim 1, wherein the second population of cells expresses a heterogeneous repertoire of immune cell receptors.

4. A method of sequencing mRNAs of a doublet of cells, the method comprising:
isolating a doublet comprising a first cell and a second cell that form an immunological synapse between an antigen expressed on the first cell surface and an immune cell receptor expressed on the second cell surface;
contacting mRNA from the first and second cells of the isolated doublet, wherein an mRNA from the first cell encodes the antigen and an mRNA from the second cell encodes the immune cell receptor; and
sequencing the mRNAs from the first and second cells.

5. The method of claim 4, further comprising:
contacting the mRNA of the isolated doublet with a solid phase comprising a first oligonucleotide comprising a first sequence complementary to the mRNA encoding the antigen and a second oligonucleotide comprising a second sequence complementary to the mRNA encoding the immune cell receptor; and
sequencing mRNAs that hybridize to the solid phase.

6. The method of claim 5, wherein (a) the first sequence is complementary to coding sequence for the antigen, (b) the second sequence is complementary to coding sequence for the immune cell receptor, or both (a) and (b).

7. The method of claim 4, further comprising forming the doublet by co-incubating:
a first population of cells each expressing an antigen, wherein the antigen of any two cells of the first population can be the same or different; and
a second population of cells each expressing an immune cell receptor that binds the antigen, wherein the immune cell receptor of any two cells of the second population can be the same or different,
thereby forming a population of doublets comprising the doublet.

8. The method of claim 5, wherein the first oligonucleotide, the second oligonucleotide, or both further comprise an oligo dT sequence.

9. The method of claim 5, wherein the solid phase comprises beads.

10. The method of claim 5, wherein the sequencing is performed by an emulsion-based bead sequencing.

11. The method of claim 7, wherein the cells of the second population are lymphocytes.

12. The method of claim 11, wherein the lymphocyte is selected from the group consisting of B cells, CD4 T cells, CD8 T cells, Gamma-Delta T cells, NK T cells, and any hematopoietically-derived cells.

13. The method of claim 5, further comprising isolating additional doublets from the population of doublets and sequencing mRNAs encoding the antigen and the immune cell receptor from the additional doublets, thereby obtaining sequence information of a repertoire of antigens and a repertoire of immune cell receptors that bind each other.

14. The method of claim 7, wherein the first population of cells expresses a heterogeneous repertoire of antigens.

15. The method of claim 7, wherein the second population of cells expresses a heterogeneous repertoire of immune cell receptors.

16. A kit for obtaining sequence information of an antigen and an immune cell receptor that binds to the antigen, the kit comprising:
a vector for expressing an antigen on the surface of a cell, the vector comprising:
a sequence encoding a type II transmembrane sequence;
an insertion site configured to contain a sequence encoding the antigen,
wherein the sequence encoding a type II transmembrane sequence is 5' to the insertion site; and
a solid phase comprising a first oligonucleotide comprising a sequence complementary to an antigen mRNA and a second oligonucleotide comprising a sequence complementary to an immune cell receptor mRNA.

17. The kit of claim 16, wherein the vector is a DNA vector or an RNA vector.

18. The kit of claim 16, wherein the sequence complementary to the antigen mRNA or immune cell receptor mRNA comprises a sequence complementary to a portion of mRNA encoding the antigen or a portion of mRNA encoding the immune cell receptor.

19. The kit of claim 16, wherein (a) the first oligonucleotide further comprises an oligo dT sequence, (b) the second oligonucleotide further comprises an oligo dT sequence, or both (a) and (b).

20. The kit of claim 16, wherein the solid phase comprises beads.

21. The kit of claim 16, wherein the insertion site comprises the sequence encoding the antigen.

22. The kit of claim 16, wherein the vector and solid phase are configured for sequencing.

* * * * *